(12) United States Patent  
Lippard et al.

(10) Patent No.: US 7,615,377 B2  
(45) Date of Patent: Nov. 10, 2009

(54) FLUORESCEIN-BASED METAL SENSORS

(75) Inventors: Stephen J. Lippard, Cambridge, MA (US); Elizabeth Marie Nolan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 981 days.

(21) Appl. No.: 10/928,924

(22) Filed: Aug. 27, 2004

(65) Prior Publication Data

US 2005/0112769 A1  May 26, 2005

Related U.S. Application Data

(60) Provisional application No. 60/500,807, filed on Sep. 5, 2003.

(51) Int. Cl.
*G01N 21/64* (2006.01)
*G01N 33/20* (2006.01)
*C07D 311/82* (2006.01)
*C07D 311/88* (2006.01)

(52) U.S. Cl. .................. 436/166; 422/55; 422/82.08; 436/73; 436/76; 436/77; 436/79; 436/80; 436/81; 436/82; 436/83; 436/84; 436/173; 549/223; 549/224; 549/225; 549/226

(58) Field of Classification Search .................. 544/1, 544/36, 58.1, 101, 102, 344; 546/102; 435/6; 436/73, 7, 172, 76, 77, 79–84, 166, 173; 540/1; 549/26, 228, 265, 223–226; 562/466; 422/55, 82.08

See application file for complete search history.

(56) References Cited

U.S. PATENT DOCUMENTS

| 4,510,251 A | 4/1985 | Kirkemo et al. ............. 436/536 |
| 4,614,823 A | 9/1986 | Kikermo et al. ............. 544/300 |
| 5,026,783 A | 6/1991 | Grubbs et al. ............. 525/326.1 |
| 5,284,934 A | 2/1994 | Allen, Jr. ..................... 530/370 |
| 5,346,670 A | 9/1994 | Renzoni et al. ................ 422/52 |
| 5,409,591 A | 4/1995 | Baker et al. .................. 204/425 |
| 5,418,366 A | 5/1995 | Rubin et al. ............. 250/338.5 |
| 5,453,220 A | 9/1995 | Swager et al. ............... 252/582 |
| 5,466,350 A | 11/1995 | Baker et al. ............ 204/153.14 |
| 5,519,147 A | 5/1996 | Swager et al. .................. 549/59 |
| 5,565,075 A | 10/1996 | Davis et al. ................. 204/412 |
| 5,580,433 A | 12/1996 | Baker et al. ................. 204/425 |

(Continued)

FOREIGN PATENT DOCUMENTS

EP          0 201 751 A2      11/1986

(Continued)

OTHER PUBLICATIONS

Atar, D. et al., "Excitation-Transcription Coupling Mediated by Zinc Influx Through Voltage-dependent Calcium Channels", J. Biol. Chem 1995, 270:2473-2477.

(Continued)

*Primary Examiner*—Jill Warden
*Assistant Examiner*—Paul S Hyun
(74) *Attorney, Agent, or Firm*—Foley Hoag LLP

(57) ABSTRACT

The present invention is directed, in part, to fluorescein-based ligands for detection of metal ions, and methods of making and using the same.

13 Claims, 24 Drawing Sheets

U.S. PATENT DOCUMENTS

| | | | | |
|---|---|---|---|---|
| 5,582,170 | A | 12/1996 | Soller | 128/634 |
| 5,603,820 | A | 2/1997 | Malinski et al. | 205/781 |
| 5,721,365 | A | 2/1998 | Keefer et al. | 544/382 |
| 5,756,771 | A | 5/1998 | Mattingly | 549/223 |
| 5,986,094 | A | 11/1999 | Ghoshal et al. | 544/230 |
| 6,002,817 | A | 12/1999 | Kopelman et al. | 385/12 |
| 6,013,802 | A | 1/2000 | Hoyland et al. | 546/18 |
| 6,051,207 | A | 4/2000 | Klaveness et al. | 424/9.1 |
| 6,063,637 | A | 5/2000 | Arnold et al. | 436/94 |
| 6,083,758 | A | 7/2000 | Imperiali et al. | 436/73 |
| 6,100,096 | A | 8/2000 | Bollinger et al. | 436/116 |
| 6,160,255 | A | 12/2000 | Sausa | 250/227.24 |
| 6,323,309 | B1 | 11/2001 | Swager et al. | 528/380 |
| 6,623,870 | B1 | 9/2003 | Epstein et al. | 428/690 |
| 6,635,415 | B1 | 10/2003 | Bollinger et al. | 435/4 |
| 6,636,652 | B1 | 10/2003 | Kopelman et al. | 385/12 |
| 2002/0040805 | A1 | 4/2002 | Swager | 174/110 |
| 2002/0106697 | A1* | 8/2002 | Lippard et al. | 435/7.2 |
| 2002/0146726 | A1* | 10/2002 | Matray et al. | 435/6 |
| 2002/0150697 | A1 | 10/2002 | Swager et al. | 428/1.1 |
| 2002/0182740 | A1 | 12/2002 | Noire et al. | 436/106 |
| 2003/0008405 | A1 | 1/2003 | Lippard et al. | 436/73 |
| 2003/0178607 | A1 | 9/2003 | Swager et al. | 252/582 |

FOREIGN PATENT DOCUMENTS

| | | |
|---|---|---|
| EP | 0 297 303 A2 | 1/1989 |
| WO | WO 96/40665 | 12/1996 |

OTHER PUBLICATIONS

Barker et al., "Cellular Applications of a Sensitive and Selective Fiber-Optic Nitric Oxide Biosensor Based on a Dye-Labeled Heme Domain of Soluble Guanylate Cyclase", *Anal. Chem.* 71: 2071-2075 (1999).

Barker et al.; "Development and Cellular Applications of Fiber Optic Nitric Sensors Based on a Gold-Absorbed Fluorophore", *Anal. Chem.* 70:4902-4906 (1998).

Barker, et al., "Fiber-Optic Nitric Oxide-Selective Biosensors and Nasnosensors", *Anal. Chem.* 70: 971-976 (1998).

Barker et al., "Ratiometric and Fluorescence-Lifetime-Based Biosensors Incorporating Cytochrome C' and the Detection of Extra- and Intracellular Macrophage Nitric Oxide ", *Anal. Chem.* 71:1767-1772 (1999).

Bätz et al.; "A Novel Method for Detecting Nitric Oxide (NO) by Formation of Fluorescent Products Based on Chelectropic Spin Traps ", Angew. Chem. Int. Ed. Engl. 36: 1501-1503 (1997).

Belgodere, E. et al., "Imidazolecarboxylic Acids and Their Derivatives, Synthesis of 10H-Imidazo[1,5-a]pyrido[1,2-d]pyrazin-10-one, A Novel Ring System", Heterocycles 1985, 23, 2, 349-355.

Bergonzi et al.; "Molecular Switches of Fluorescence Operating Through Metal Centred Redox Couples", Coord. Chem. Rev. 170: 31-46 (1998).

Borsari et al.; "Amide Nitrogen Co-ordination of CoII and Ni II in Ternary 2,2'-Bipyridine-containing systems. A Solution and Solid-state Study", *J. Chem. Soc,*. Dalton Trans. pp. 4201-4205 (1996).

Buchen et al.; "Copper Complexes of a p-phenylenediamine-based bis (tridentate) Ligand ", J. Chem. Soc. Dalton Trans. pp. 2697-2703, (1997).

Budde, T. et al.; "Imaging Free Zinc In Synaptic Terminals in Live Hippocampal Slices", Neuroscience 1997, 79, 347-358.

Burdette, S. C. et al., "Fluorescent Sensors for $Zn^{+2}$ Based on a Fluorescein Platform: Synthesis, Properties and Intracellular Distribution", J. Am. Chem Soc., 2001, 123, 7831-7841.

Burdette, S. C., "Investigation of Zinc Metalloneurochemistry with Fluorescent Sensors Based on Fluorescein Platforms", Ph.D. Thesis, MIT, Oct. 2002.

Burdette, S. C. et al.; "The Rhodafluor Family. An Initial Study of Potential Ratiometric Fluorescent Sensors for $Zn^{2+}$", Inorg. Chem. 2002, 41, 6816-6823.

Burton, H., et al., "Fluorescein Dyes Derived from 2-Methylresorcinol", J. Soc. Chem. Ind. London 1948: 67: 345-347.

Canzoniero, L. M. T. et al., "Measurement of Intracellular Free Zinc in Living Neurons", Neurobiology of Disease 1997, 4, 275-279.

Castresana et al.; "Structure of Diaquabis (4-methyl -N-8-quinolylbenzenesulphonamido-N,N')cobalt(II)- Acetone (1/1), [Co(C 16 H13 N2 O2 S)2 (H2 O)2]. C3 H6 O", Acta Cryst. C, 40: 763-765, (1984).

Chenier et al.; "Chiral Tropocoronands: Synthesis and Metal Complex Formation," *Tetrahedron Lett.*, 38:7341-7344 (1997).

Choi, D. W. et al., "Zinc and Brain Injury", Ann. Rev. Neurosci. 1998, 21: 346-375.

Copeland and Miller, "A Chemosensor-Based Approach to Catalyst Discovery in Solution and on Solid Support", J. Am. Chem. Soc. 121: 4306-4307 (1999).

Cuajungco, M. P. et al., "Zinc Metabolism in the Brain: Relevand to Human Neurodegenerative Disorders", Neurobiology of Disease 1997, 4, 137-169.

Czarnick, A. W., "Desperately Seeking Sensors", Curr. Biol 1995, 2: 423-428.

Da Mota, M. M. et al., "The Co-ordination Number of Transition-Metal Ions. Part VII: An Evaluation of Steric Factors in the Stabilisation of High-spin Five-co-ordinate Nickel (II) Complexes of Multidendate α-Pyridyl Ligands", J. Chem. Soc. (A) 1969, 2036-2042.

De Silva, A. P. et al., "Signaling Recognition Events with Fluorescent Sensors and Switches", Chem. Rev. 1997, 97: 1515-1566.

Del Zotto et al.; "Five Coordinate Diphosphine Complexes of the {CoNo}8 Group, and Their Disproportionation Reactions to Cobalt (III) and {Co(NO)2 } 10 Derivatives", Inorganica Chimica Acta, 171:61-69, (1990).

Dias et al.; "Synthesis and Characterization of Lithium, Zirconium, and Hafnium Derivatives of N-Isopropyl-2-(isopropylamino)troponiminate", Inorg. Chem. 35: 6074-6079, (1996).

Doyle and Hoekstrta; "Oxidation of Nitrogen Oxides by Bound Dioxygen in Hemoproteins", J. Inorg. Biochem. 14(4): 351-358, (1981).

Eaton et al.; "Synthesis and Magnetic Resonance Studies of Some Paramagnetic Transition Metal Aminotroponiminates", Inorganic Chemistry, 7(10): 2040-2046, (1968).

Ebadi, M. et al., "Amino Acid Composition, Immunoreactivity, Sequence Analysis, and Function of Bovine Hippocampal Metallothionein Isoforms", J. Neurochem. 1996, 66: 2121-2127.

Ebadi, M. et al., "Expression and Regulation of Brain Metallothionein", Neurochem. Int. 1995, 27: 1-22.

Ebadi, M., "Metallothioneins and Other Zinc-Binding Proteins in Brain", Methods Enzymol. 1991, 205: 363-387.

Evans, R. L. et al., "Synthesis of γ-Aminobutyryl-γ-aminobutyric Acid", Org. Chem. 1959, 24: 863-864.

Fabbrizzi et al.; "Controllable Intramolecular Motions That Generate Fluorescent Signals for a Metal Scorpionate Complex", Angew. Chem. Int. Ed. 37(6): 800-802, (1998).

Fabbrizzi et al.;"Transition Metals as Switches", Acc. Chem. Res. 32: 846-853, (1999).

Fahrni, C. J. et al., "Aqueous Coordination Chemistry and Quinoline-Based Fluorescence Probes for the Biological Chemistry of Zinc", J. Am. Chem. Soc. 1999, 121: 11448-11458.

Feig, A. L. et al., "A Carboxylate-Bridged Non-Heme Diiron Dinitrosyl Complex", Inorg. Chem. 1996, 25: 6892-6898.

Flack D. H.; "On Enantiomorph-Polarity Estimation", Acta Cryst. A39:876-881, (1983).

Franz et al.; "Metal-Based NO Sensing by Selective Ligand Dissociation", Angew. Chem. Int. Ed. 39(12): 2120-2122, (2000).

Frederickson, C. J., et al., "A quinoline fluorescence method for visualizing and assaying the histochemically reactive zinc (bouton zinc) in the brain", J. Neurosci. Meth. 1987,20,91-103.

Frederickson, C. J., "Neurobiology of Zinc and Zinc-Containing Neurons", Int. Rev. Neurobiol., 1989, 31: 145-238.

Frederickson, C. J., et al., "Zinc-Containing Neurons", Biol Signals 1994; 3: 127-139.

Furchgott, F. R.; "Endothelium-Derived Relaxing Factor: Discovery, Early Studies, and Identification as Nitric Oxide (Nobel Lecture)", Angew. Chem. Int. Ed. 38: 1870-1880, ( 1999).

Godwin, H. A., et al., "A Fluorescent Zinc Probe Based on Metal-Induced Peptide Folding", J. Am. Chem. Soc. 1996, 118: BI6514-6515.

Goral, Vasiliy et al., "Double-level "orthogonal" dynamic combinatorial libraries on transition metal template", *Proceedings of the National Academy of Sciences*, vol. 98, No. 4, pp. 1347-1352 (2001).

Gruenwedel, D. W., "Multidentate Coordination Compounds. Chelating Properties of Aliphatic Amines Containing α-Pyridyl Residues and Other Aromatic Ring Systems as Donor Groups", Inorg. Chem. 1968,7: 495-501.

Haider et al., "X-ray Crystal Structures of Metal -Saccharin Complexes of General Formula [M(C7H4NO3S)2(H2O)4]. 2H2O, Where M=Fe(II), Co(II), Ni(II) and Cu(II)", Inorganica Chimica Acta,72: 21-27 (1983).

Harrison, N. L., et al., "$Zn^{2+}$: an Endogenous Modulator of Ligand- and Voltage-gated Ion Channels", Neuropharmacology 1994, 33: 935-952.

Hartwig, F. J. "Carbon Heteroatom Bond-Forming Reductive Eliminations of Amines, ethers, and Sulfides", Acc. Chem. Res. 31: 852-860, (1998).

Hirano, T., et al., "Highly Zinc-Selective Fluorescent Sensor Molecules Suitable for Biological Applications", J. Am. Chem. Soc. 2000, 122: 12399-12400.

Hörlein, U. ; "Zur Kenntnis Der Tetrahydrocarbolin-Verbin-Dungen (I. Mitteil. )", Chemische Berichte, 87(4): 463-472, (1954).

Houser, R. P. et al., "Structural Characterization of the First Example of a Bis(μ-thiolato)dicopper(II) Complex. Relevance to Proposals for the Electron Transfer Sites in Cytochrome c Oxidase and Nitrous Oxide Reductase", J. Am. Chem Soc. 1995, 117: 10745-10746.

Huang, E. P., "Metal Ions and Synaptic Transmission: Think Zinc", Proc. Natl. Acad. Sci. Dec. 1997, 94: 13386-13387.

Ignarro, J. L., Nitric Oxide: A Unique Endogenous Signaling Molecules in Vascular Biology (Nobel Lecture ), Angew. Chem. Int. Ed. 38: 1882-1892,(1999).

Jia et al., "S-nitrosohaemoglobin: a Dynamic Activity of Blood Involved in Vascular Control", Nature 380: 221-226 (Mar. 21, 1996).

Jones, L. J., "Quenched Bodipy Dye-Labeled Casein Substrates for the Assay of Protease Activity by Direct Fluorescence Measurement", Anal. Biochem. 251:144-152 (1997).

Katayama et al.; Design, Synthesis and Characterization of a Novel Fluorescent Probe for Nitric Oxide (Nitrogen Monoxide), Analytica Chimica Acta 365: 159-167 (1998).

Kikuchi, M. S. et al., "A Novel, Cell-Permeable, Fluorescent Probe for Ratiometric Imaging of Zinc Ion", J. Am. Chem. Soc. 2002, 124: 10650-10651.

Koike et al., "A Novel Biomimetic Zinc(II)-Fluorophore, Dansylamidoethyl-Pendant Macrocyclic Tetraamine 1,4,7,10-Tetraazacyclododecane (Cyclen)", J. Am. Chem. Soc. 118: 12696-12703 (1996).

Koike et al.; "The First Anionic Sulfonamide-Binding Zinc (II) Complexes with a Macrocyclic Triamine: Chemical Verification of the Sulfonamide Inhibition of Carbonic Anhydrase", J. Am. Chem. Soc. 114:7338-7345 (1992).

Kojima et al.; "Detection and Imaging of Nitric Oxide with Novel Fluorescent Indicators: Diaminofluoresceins", Anal. Chem. 70: 2446-2453 (1998).

Kojima et al.; "Development of a Fluorescent Indicator for Nitric Oxide Based on the Fluorescein Chromophore", Chem. Pharm. Bull. 46(2): 373-375 (1998).

Kojima et al., "Fluorescent Indicators for Imaging Nitric Oxide Production", Angew. Chem. Int. Ed. 38(21): 3209-3212 (1999).

Kovacs, Z. et a., "A General Synthesis of Mono- and Disubstituted 1,4,7-Triazacycloonoanes", Tet. Lett. 1995, 51: 9269-9272.

Lancaster, Jr. R. J. "A Tutorial on the Diffusibility and Reactivity of Free Nitric Oxide", Nitric Oxide: Biology and Chemistry, 1(1): 28-30, (Feb. 1997).

Mahadevan, I. B. et al., "The Synthesis of Zinquin Ester and Zinquin Acid, Zinc(II)-Specific Fluorescing Agents for Use in the Study of Biological Zinc (II)", Aust. J. Chem. 1996, 49: 561-568.

Malinski et al.; "Diffusion of Nitric Oxide in the Aorta Wall Monitored In Situ by Porphyrinic Microsensors", Biochemical and Biophysical Research Communications, 193(3):1076-1082 (Jun. 30, 1993).

McBryde, W. A. E.,"Spectrophotometric Determination of Equilibrium Constants in Solution", Talanta, 21: 979-1004 (1974).

McClellan and Benson;, "Iron (II) Chelates of N,N'- Disubstituted Aminotroponeimines", Journal of the American Chemical Society 88(22): 5165-5169 (Nov. 20, 1966).

Meineke et al; "Cheletropic Traps for the Fluorescence Spectroscopic Detection of Nitric Oxide (Nitrogen Monoxide)in Biological Systems", Chem. Europ. J., 5(6): 1738-1747 (1999).

Minta et al.; "Fluorescent Indicators for Cytosolic Calcium Based on Rhodamine and Fluorescein Chromophores", the Journal of Biological Chemistry, 264(14): 8171-8178 (May 15, 1989).

Mizukami, S. et al., "Imaging of caspase-3 activation in HeLa cells stimualted with etoposide using a novel fluorescent probe", FEBS Lett 1999, 453: 356-60.

Murad, F. ; Discovery of Some of the Biological Effects of Nitric Oxide and its Role in Cell Signaling (Nobel Lecture), Angew Chem. Int. Ed. 38: 1856-1868, (1999).

Nasir, M. S. et al., "The chemical cell biology of zinc: structure and intracellular fluorescence of a zinc-quinolinesulfonamide complex", JBIC 1999, 4: 775-783.

Nozoe et al.; "Synthesis of 2-Aminotrope Oximes and 2-Alkoxytropone", *J. Chem. Research* (S), pp. 362-363 (1997).

Packard, B. Z. et al., "Characterization of fluorescence quenching in bifluorophoric protease substrates", *Biophys. Chem.*, 67:167-176 (1997).

Packard, B. Z. et al., "Profluorescent protease substrates: Intramolecular dimers described by the exciton model", *Proc. Natl. Acad. Sci. USA* 93:11640-11645 (1996).

Palmiter, R. D. et al., "Cloning and functional characterization of a mammalian zinc transporter that confers resistance to zinc", EMBO J. 1995, 14: 639-649.

Palmiter, R. D. et al., "MT-III, a brain-specific member fo the metallothionein gene family", Proc. Natl. Acad. Sci. USA 1992, 89: 6333-6337.

Palmiter, R. D. et al., "ZnT-2, a mammalian protein that confers resistance to zinc by facilitating vesicular sequestration", EMBO J. 1996, 15: 1874-1791.

Palmiter, R. D. et al., "ZnT-3, a putative transporter of zinc into synapse vesicles", Proc. Natl. Acad. Sci. USA 1996, 93: 14934-14939.

Pfeiffer et al.; "Nitric Oxide: Chemical Puzzles Posed by a Biological Messenger", Angew. Chem. Int. Ed. 38: 1714-1731, (1999).

Poutney, D.L. et al., "Isolation, primary structures and metal binding properties of neuronal growth inhibitory factor (GIF) from bovine and equine brain", FEBS Lett. 1994, 345: 193-197.

Prasad, J. S., et al., "Synthesis of Gadolinium (±)-10-(1-Hydroxypropan-2-y1)-1,4,7,10-tetraazacyclododecane-1,4,7-triyltriacetate via Tribenzyl 1,4,7,10-Tetraazacyclododecane-1,4,7-tricarboxylate", J. Chem. Soc. Perkin Trans. 1991, 3329-3332.

Romary, J. K. et al., "New 2-Pyridyl Polyamines. Synthesis, Spectra, and Proton Dissociation Constants", J. Chem. Soc. (C) 1968, 2884-2887.

Sato et al.; "Convenient Synthesis of N,N,N',N'-Tetrakis (2-Pyridylmethyl)-α, ω-alkanediamines Using a Phase-Transfer Catalyst", Synthesis, pp. 539-540, (Jun. 1992).

Sen, R. N. et al., "Aldehydofluorescein and Dyes Derived from it", J. Indian Chem. Soc. 1929,6: 505-516.

Sen, R. N. et al., "Aldehydo-phenolphthalien and Dyes derived from it", J. Indian Chem. Soc. 1929, 6: 53-63.

Shaughnessy et al.; "A Fluorescence-Based Assay for High-Throughput Screening of Coupling Reactions. Application to Heck Chemistry", J. Am. Chem. Soc. 121: 2123-2132, (1999).

Slomianka, L., "Neurons of Origin of Zinc-Containing Pathways and the Distribution of Zinc-Containing Boutons in the Hippocampal Region of the Rat", Neuroscience 1992, 48: 325-352.

Smith et al.; "The Design and Properties of a Series of Calcium Indicators Which Shift from Rhodamine-like to Fluorescein-like Fluorescence on Binding Calcium", J. Chem. Soc. Perkin Trans. 2, pp. 1195-1204, (1993).

Steinhuebel and Lippard, "Synthesis and Characterization of (Aminotroponiminato)titanium (IV) Dialkyl Complexes: Control of Reactivity by Ligand Design", Organometallics, 18: 3959-3961, (1999).

Steinhuebel and Lippard; "Synthetic and Structural Studies of Titanium Aminotroponiminate Complexes", Inorg. Chem. 38: 6225-6233, (1999).

Sumner, J. P. et al., "A Fluroescent Pebble Nanosensor for Intracellular Free Zinc", Analyst 2002, 127: 11-16.

Sun et al.; "Synthesis of Fluorinated Fluoresceins" J. Org. Chem. 62: 6469-6475, (1997).

Takakusa, H. et al., "A Novel Design Method of Rationmetric Fluorescent Probes Based on Fluorescence Resonance Energy Transfer Switching by Spectral Overlap Integral", Che. Eur. J. 2003, 9(7): 1479-1485.

Takakusa, H. et al., "Intramolecular Fluorescence Resonance Energy Transfer System with Coumarin Donor Included in β-Cyclodextrin", Anal. Chem. 2001, 73(5): 939-942.

Tanaka, M. et al., "Synthesis and Metal-Ion Binding Properties of Monoazathiacrown Ethers", J. Org. Chem. 2001, 66: 7008-7012.

Thompson, R. B. et al., "Expanded Dynamic Range of Free Zind Ion Determination by Fluorescence Anisotropy", Anal. Chem. 1998, 70: 1749-1754.

Thompson, R. B. et al., "Fluorescence microscopy of stimulated Zn(II) release from organotypic cultures of mammalian hippocampus using a carbonic anhydrase-based biosensor system", J. Neuro. Meth. 2000, 96: 35-45.

Trevin, S. et al.,"Electrochemical and Spectrophotometric Study of the behavior of Electropolymerized Nickel Porphyrin Films in the Determination of Nitric Oxide in Solution", Talanta, 43: 303-311(1996).

Tsien, R. Y.; "Fluorescent Probes of Cell Signaling", Ann. Rev. Neurosci., 12:227-253, (1989).

Tsien, R. Y., "Fluorescent and Photochemical Probes of Dynamic Biochemical Signals inside Living Cells", *Am. Chem. Soc.*, 130-146 (1993).

Tsien, R. Y.; "New Calcium Indicators and Buffers with High Selectivity Against Magnesium and Protons: Design, Synthesis, and Properties of Prototype Structures", Biochemistry 19: 2396-2404, (1980).

Tsuji, S. et al., "Molecular cloning of human growth inhibitory factor cDNA and its down-regulation in Alzheimer's disease", EMBO J. 1992, 11: 4843-4850.

Uchida, Y. et al., "The Growth Inhibitory Factor That Is Deficient in the Alzheimer's Disease Brain Is a 68 Amino Acid Metallothionein-like Protein", Neuron 1991, 7: 337-347.

Uhlig and Döring "Zum Verhalten von Cobalt(II und Eisen (III) bei der Flüssig-Flüssig-Extraction mit Pyridylsubstituierten Benzensulfon-amiden", Z. Anorg. Allg. Chem., 492:52-62, (1982).

Valeur, B. et al., "Tuning of Photoinduced Energy Transfer in a Bichromophoric Coumarin Supermolecule by Cation Binding", J. Phys. Chem. 1992, 96: 6545-6549.

Vallee, B. L. et al., "The Biochemical Basis of Zinc Physiology", Physiol. Rev. 1993, 73: 79-118.

von Anderegg et al.; "14. Pyridinderivate als Komplexbildner. XI [1]). Die Thermodynamik der Metallkomplexbildung mit Bis-, Tris- und Tetrakis[(2-pyridyl)methyl]-aminen", Helvetica Chimica Acta, 60: 123-140, (1977).

Walkup, G. K. et al., "A New Cell-Permeable Fluorescent Probe for $Zn^{2+}$", J. Am. Chem. Soc. 2000, 122: 5644-5645.

Walkup, G. K. et al., "Fluorescent Chemosensors for Divalent Zinc Based on Zinc Finger Domains. Enhanced Oxidative Stability, Metal Binding Affinity, and Structural and Functional Characterization", J. Am. Chem. Soc. 1997, 119: 3443-3450.

Walkup, G. K. et al., "Stereoselective Synthesis of Fluorescent α-Amino Acids Containing Oxine (8-Hydroxyquinoline) and Their Peptide Incorporation in Chemosensors for Divalent Zinc", J. Org. Chem. 1998, 63: 6727-6731.

Wang, Fen et al., "Tuning of Binding Selectivity: Metal Control of Organic Guest Binding and Allosteric Perturbation of Fluorescent Metal Sensor", *J. Org. Chem.*, vol. 64, pp. 8922-8928 (1999).

Wolf, H. U., "Divalent Metal Ion Buffers with Low pH-Sensitivity", Experientia 1973, 29: 214-249.

Wolfe and Buchwald; "Scope and Limitations of the Pd/BINAP-Catalyzed Amination of Aryl Bromides", J. Org. Chem. 65: 1144-1157, (2000).

Wolfe et al.; "Simple Efficient Catalyst System for the Palladium-Catalyzed Amination of Aryl Chlorides, Bromides, and Triflates", J. Org. Chem. 65: 1158-1174, (2000).

Zalewski, P. D. et al., "Correlation of apoptosis with change in intracellular labile Zn(II) using Zinquin [(2-methyl-8-p-Toluenesulphonadmido-6-quinolyloxy)acetic acid], a new specific fluorescent probe for Zn(II)", Biochem. J. 1993, 296: 403-408.

Zask et al.; "Syntheses and Spectral Properties of Tropocoronands, a New Class of Versatile Metal-Complexing Macrocycles Derived from Aminotropone Imines", Inorg. Chem. 25: 3400-3407, (1986).

Zhang and Buchwald, "Efficient Synthesis of N-Aryl-Aza-Crown Ethers Via Palladium-Catalyzed Amination", J. Org. Chem. 65: 8027-8031, (2000).

Zlokarnik, G. et al., "Quantitation of Transcription and Clonal Selection ofSingle Living Cells with β-Lactamase as Reporter", Sicence 1998, 279: 84-88.

* cited by examiner

Fluorescence dependence on pH for Sensor #2

MS4

Figure 20. Synthesis of Mercury Sensor MS5
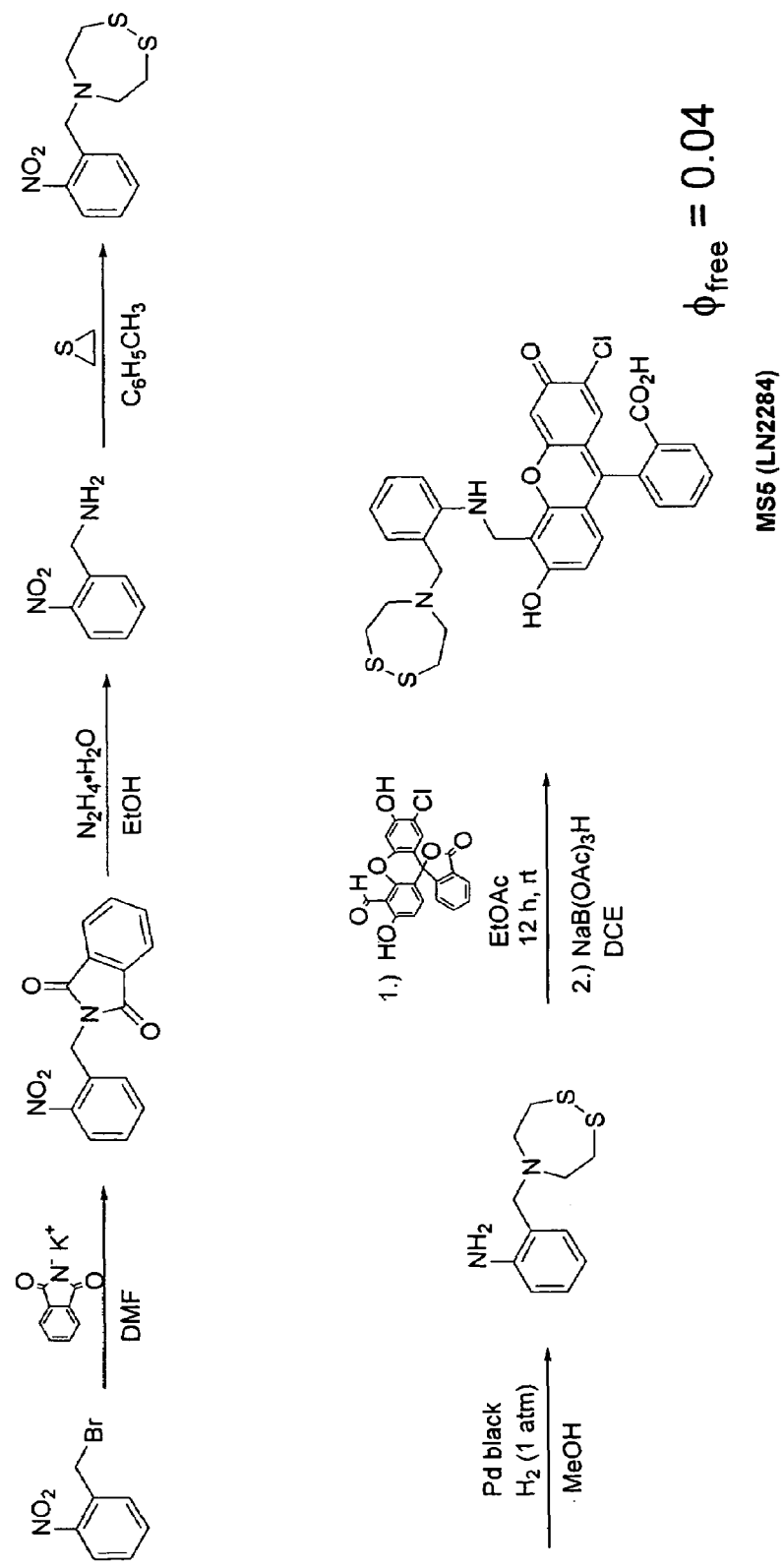

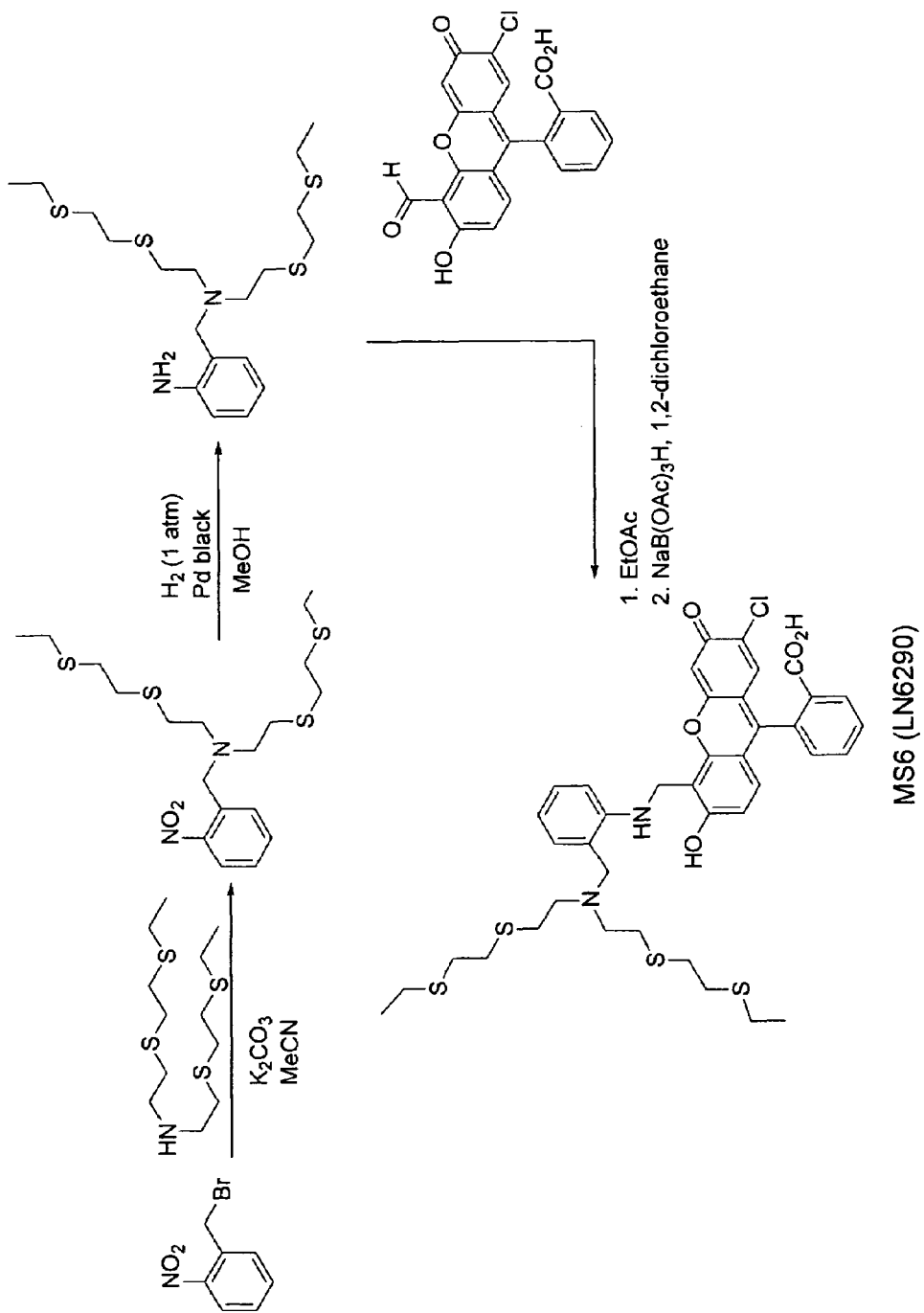
Figure 21. Synthesis of Mercury Sensor MS6

Figure 22. Response of Sensor MS6 to Hg(II)
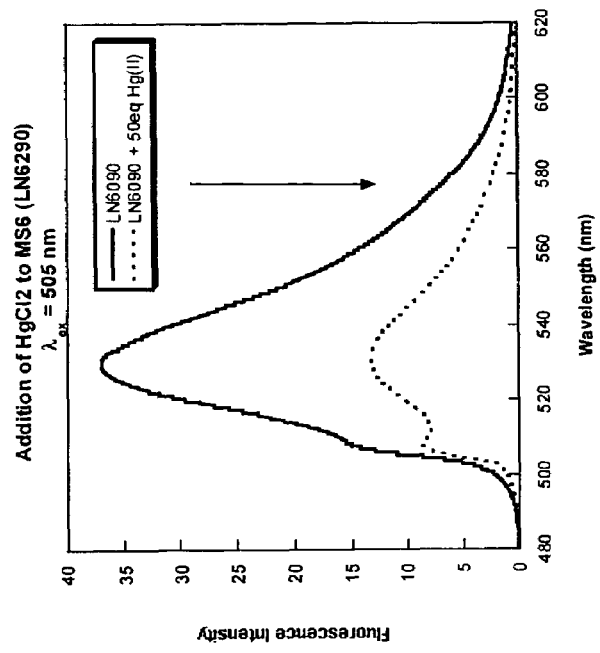
MS6 (LN6290)
$\phi_{free} = 0.19$; $\phi_{Hg} = 0.13$
50 mM PIPES, 100 mM KCl, pH 7

Figure 23. Synthesis and Properties of Sensor MS7 (LN3156)
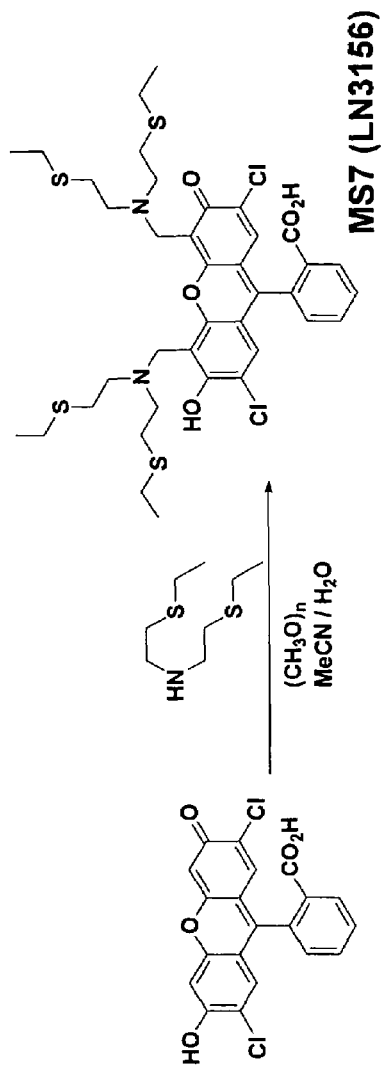
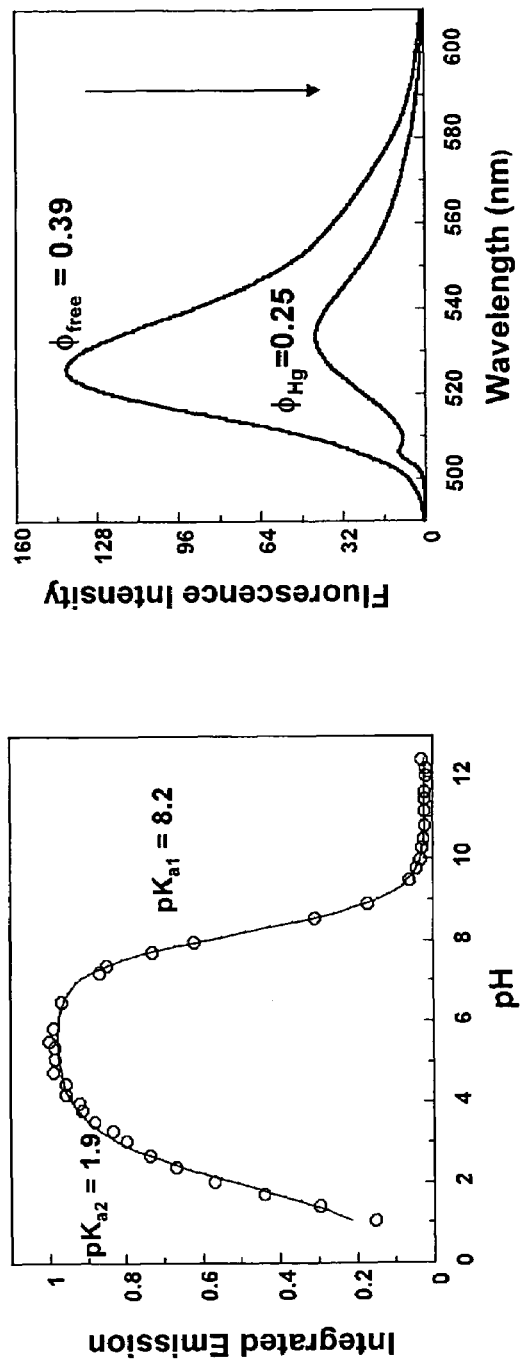

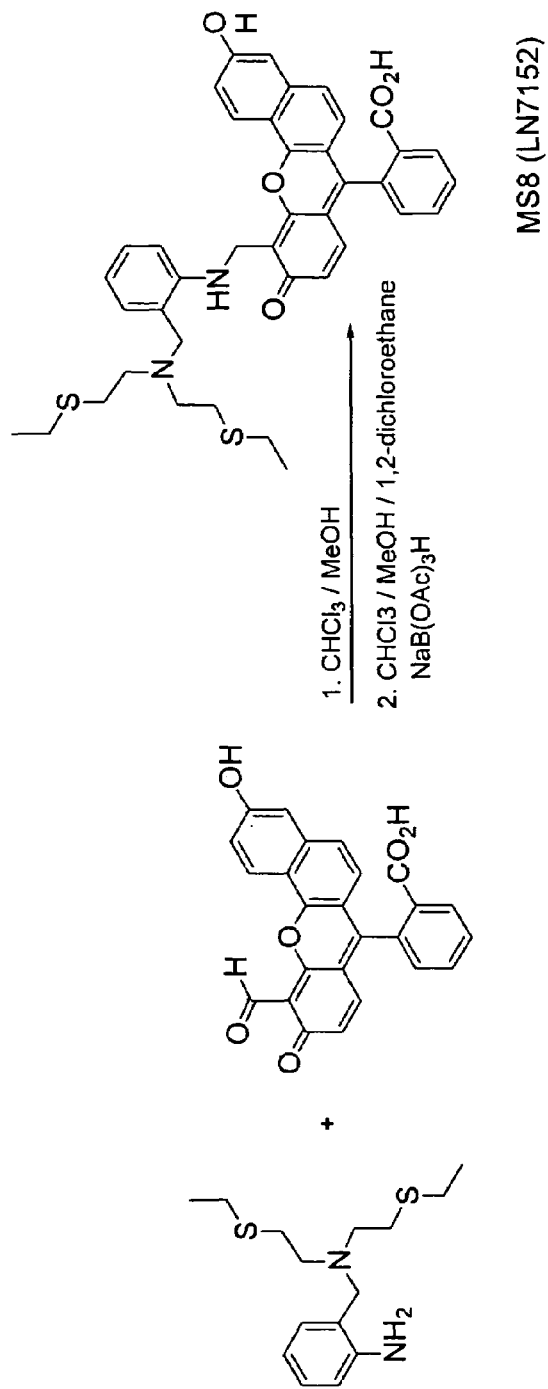
Figure 24. Synthesis of Mercury Sensor MS8

FLUORESCEIN-BASED METAL SENSORS

1. RELATED APPLICATION INFORMATION

This application claims the benefit of priority to U.S. Provisional Patent Application 60/500,807, filed Sep. 5, 2003; the specification of which is hereby incorporated by reference in its entirety.

GOVERNMENT SUPPORT

This invention was made with government support under Grant Number 1-R01-GM65519-01 awarded by the National Institutes of Health. The government has certain rights in the invention.

2. INTRODUCTION 2.1. Fluorescent Sensors

Fluorescence technology has revolutionized cell biology and many areas of biochemistry. In certain instances, fluorescent molecules may be used to trace molecular and physiological events in living cells. Certain sensitive and quantitative fluorescence detection devices have made fluorescence measurements an ideal readout for in vitro biochemical assays. In addition some fluorescence measurement systems may be useful for determining the presence of analytes in environmental samples. Finally, because certain fluorescence detection systems are rapid and reproducible, fluorescence measurements are often critical for many high-throughput screening applications.

The feasibility of using fluorescence technology for a particular application is often limited by the availability of an appropriate fluorescent sensor. There are a number of features that are desirable in fluorescent sensors, some of which may or may not be present in any particular sensor. First, fluorescent sensors should produce a perceptible change in fluorescence upon binding a desired analyte. Second, fluorescent sensors should selectively bind a particular analyte. Third, to allow concentration changes to be monitored, fluorescent sensors should have a $K_d$ near the median concentration of the species under investigation. Fourth, fluorescent sensors, especially when used intracellularly, should produce a signal with a high quantum yield. Fifth, the wavelengths of both the light used to excite the fluorescent molecule (excitation wavelengths) and of the emitted light (emission wavelengths) are often important. For analysis of water samples and other environmental samples, or for analysis of bodily fluids, the sensors are preferably soluble in water or other aqueous solutions.

If possible, for intracellular use, a fluorescent sensor should have excitation wavelengths exceeding 340 nm to permit use with glass microscope objectives and prevent UV-induced cell damage, and possess emission wavelengths approaching 500 nm to avoid autofluorescence from native substances in the cell and allow use with typical fluorescence microscopy optical filter sets. Finally, ideal sensors for intracellular use should allow for passive and irreversible loading into cells. Solubility of the sensors in water or other aqueous solution may also be a desirable characteristic of an intracellular sensor.

A limited number of fluorescent sensors possess these desirable properties. This invention is directed in part to fluorescent sensors based upon the well-known and commonly used fluorophore, fluorescein. In part, the present invention is directed to fluorescein-based ligands, and methods of making and using the same, that allow for metal ion detection, for example heavy metal ion detection, and optionally quantification of its concentration.

2.2. Heavy Metal Ion-Pollution

Heavy metal ion pollution poses severe risks for human health and the environment. For example, mercury contamination is widespread and occurs through a variety of natural and anthropogenic sources including oceanic and volcanic emission, gold mining, solid waste incineration and the combustion of fossil fuels. Once introduced into the marine environment, bacteria convert inorganic mercury into methylmercury, which enters the food chain and accumulates in higher organisms, especially in large edible fish. Methylmercury is neurotoxic and has been implicated as a cause of prenatal brain damage, various cognitive and motion disorders, and Minamata disease. Mercury, of course, is present in many aquatic environments. Further, high concentrations of lead and other heavy metals are found in soils in many urban areas. Both lead and copper contaminate soil at the Aberdeen Proving Ground in Maryland, and lead, copper, and cadmium are present in storm water runoffs entering Lakes Bay, N.J. Highly toxic thallium(I) is present in natural waters and wastewaters. The detection and remediation of such contaminated environments, or the avoidance of contamination, is an area of active interest. Further, the detection of such contaminants in edible organisms, such as fish, or the monitoring of heavy metal ion levels in workers or others living in a potentially contaminated area, is also of interest.

Our increased understanding of the deleterious effects of mercury exposure has sparked interest in the development of new tools for detecting $Hg^{2+}$ in the environment. One major challenge involves creating $Hg^{2+}$ sensors that function in aqueous media and that are highly selective for $Hg^{2+}$ against a background of competing analytes. Small synthetic molecules offer one approach to such probes. To date, a number of small molecule $Hg^{2+}$ detection methods have been examined and include colorimetric strategies, fluoroionophores, and a dithioamide functionalized lipid bilayer. Most of these systems have limitations, which include interference from other metal ions, delayed response to $Hg^{2+}$, and/or a lack of water solubility, requiring the use of organic or aqueous organic solvent mixtures. Although a fluorescent probe based on the indoaniline chromophore exhibiting selectivity for $Hg^{2+}$ in water was recently described, 25 $Hg^{2+}$binding results in a decrease of quantum yield (f) and brightness (fxe).

Further, other soft metal ions, which include heavy metal ions such as $Hg^{2+}$, are of concern because they are highly toxic and are present in a variety of waste streams that can potentially contaminate the environment if released. For example, the following soft metal ions are currently identified for regulation under RCRA/SDWA: $Cu^{2+}$, $Ag^+$, $Cd^{2+}$, $Hg^{2+}$, $Pb^{2+}$ and $Tl^+$.

In part, the present invention is directed to novel fluorescent sensors for soft metal ions such as $Hg^{2+}$ and methods for making and using the same. Certain of these sensors allow soft metal ions to be visualized or detected as described below.

3. SUMMARY OF THE INVENTION

In one aspect, the present invention is directed to fluorescein-based compositions. In part, the present invention is directed to fluorescein-based ligands, and methods of making and using the same. Such ligands may be used to detect the presence of metal ions, particularly heavy metal ions.

The subject compositions, and methods of making and using the same, may achieve a number of desirable results and features, one or more of which (if any) may be present in any particular embodiment of the present invention: (i) fluorescein-based ligands bind metal ions with a concomitant change in the fluorescence properties of the ligand, and in certain embodiments fluoresce only when a metal ion is bound and in other embodiments are quenched when a metal ion is bound; (ii) fluorescein-based ligands selectively bind a metal ion; (iii) fluorescein-based ligands have a $K_d$ near the median concentration of the metal ion under investigation allowing for concentrations of the metal ion to be determined; (iv) fluorescein-based ligands exhibit a high quantum yield upon complexation of a metal ion; (v) excitation wavelengths for fluorescein based ligands exceed 340 nm and emission wavelengths approach 500 nm; (vi) fluorescein based ligands are capable of in vivo use, and possibly also passive and irreversible loading into cells; (vii) upon binding a metal of interest, the subject ligands exhibit a shift in emission wavelength, which may be used for visualizing concentration fluctuations and the spatial distribution of dye and analyte; (viii) the subject fluorescein based ligands are soluble in aqueous solutions.

In one aspect, the present invention is directed to fluorescein based ligands:

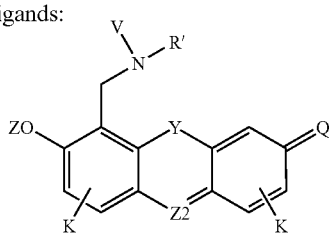

wherein, as described in greater detail below, Q is O, S, Se; K is optionally one or more substituents of the indicated aromatic ring that do not materially alter the fluorescence of the ligand as described below; V is a Lewis base; R' is H, alkyl, aryl or V, such that at least one V comprises at least one sulfur-containing moiety capable of forming one or more coordination bonds with a metal ion; Y is O, S, Se, NR, or C(CH3)3, wherein R is an alkyl and R and the methyl groups of C(CH3)2 are optionally substituted; and Z2 is N, HOOCCH$_2$CH$_2$C, HOOC—CH=CH—C, (2-carboxyphenyl)-C, and substituted derivatives thereof. If Q is —OZ, whereupon a different tautomer is obtained, Z2 varies accordingly. Upon addition to an aqueous solution containing Hg$^{2+}$ at about pH 7.0, the fluorescence of these fluorescein-based ligands may increase by at least about 5%, at least about 7%, about 10%, about 50%, about 60%, about 70%, about 80%, about 90%, about 95%, about 97%, about 98%, about 99%, about 100%, about 150%, about 200%, about 300% or even 500% or more.

Other subject ligands include:

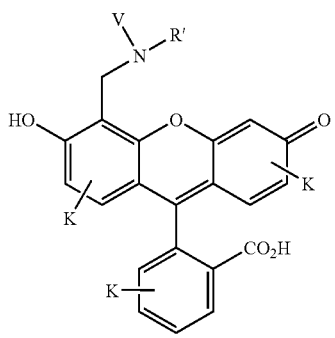

Other subject ligands include:

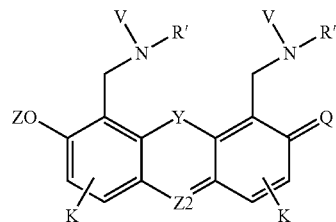

wherein the terms are as defined previously and providing that only one V need contain a sulfur moiety.

In other embodiments, the fluorescein-based ligands of the present invention have the structures described in certain of the claims below, all of which claims are hereby incorporated by reference in their entirety into this Summary to describe the present invention.

In another aspect, the subject fluorescein-based ligands may be attached to a targeting moiety to direct the ligand to a particular target. For instance, targeting of the subject ligands may allow for detection, and, optionally, quantification of the concentration of, metal ions at a target cell of interest in vivo.

In another aspect, the present invention is directed to coordination complexes comprising the subject fluorescein-based ligands complexed to one or more metal ions.

In another aspect, the present invention provides a number of methods of making the subject compositions, including the subject fluorescein-based ligands.

In another aspect, the subject invention involves methods of using the subject fluorescein-based ligands to detect, and, optionally, to quantify concentrations of, metal ions in a sample. The detection methods rely on the change observed in the fluorescence of the subject fluorescein-based ligands upon complexation with a metal ion. Any change observed, both positive and negative, and including, for example, a change in the emission wavelength, the excitation wavelength, and the quantum yield, may be used to detect metal ion complexation. The methods may be used in vitro to analyze the concentration of metal ions in a sample, for example a water or soil sample, a sample of bodily fluid such as blood, urine, or saliva, or a cellular extract. The methods may be used in vivo to detect changes in intracellular concentrations of metal ions with the appropriate fluorescein-based ligand. In addition, the present inventive methods provide for positive and negative controls.

In another aspect, the present invention is directed to methods of using the subject fluorescein-based ligands for diagnostic purposes. In certain instances, the subject compositions and methods may be used to detect, and, optionally, to quantify the concentration of, a metal ion of interest in a patient.

In another aspect, the present invention is directed to methods of using the subject fluorescein-based ligands for determining the presence of analytes in samples, including samples of environmental interest. In certain aspects, such samples may have a pH of approximately 3, 4 5, 6, 7, 8, 9, 10, 11, 12, or higher, or alternatively, when the sample is from a natural source, the pH that is naturally-occurring (e.g. a human tissue or fluid, or a soil or water sample).

In other embodiments, this invention contemplates a kit including subject compositions, and optionally instructions for their use. Uses for such kits include, for example, diagnostic applications.

These embodiments of the present invention, other embodiments, and their features and characteristics, will be apparent from the description, drawings and claims that follow.

4. BRIEF DESCRIPTION OF THE DRAWINGS

FIG. 1 depicts the synthesis of $Hg^{2+}$ sensor 1 (Formula 1). This sensor is alternatively referred to throughout the present application as "sensor 1" or "MS1" or "ZS1".

FIG. 2 depicts the fluorescence response of sensor 1 to $Hg^{2+}$. Conditions: 1 mM probe; 0-3 equivalents of $Hg^{2+}$ added; (50 mM CABS, 100 mM KCl, pH 11); and $l_{ex}$=504 nm. Fluorescence spectrum shows ~6-fold increase in integrated emission upon addition of $Hg^{2+}$ at pH 11 and ~15% increase in integrated emission in the presence of 2 ppb of $Hg^{2+}$ (2 ppb is the EPA limit for inorganic $Hg^{2+}$ in drinking water). Quantum yield and epsilon for sensor 1:pH 7:$F_{free}$=0.27 ($e_{497\ nm}$=61,600 $M^{-1}$ $cm^{-1}$), $F_{Hg}{}^{2+}$=0.27 ($e_{500\ nm}$=69,000 $M^{-1}$ $cm^{-1}$); pH 11:$F_{free}$=0.07 ($e_{504\ nm}$=60,800 $M^{-1}$ $cm^{-1}$), $F_{Hg}{}^{2+}$=0.24 ($e_{507\ nm}$=78,300 $M^{-1}$ $cm^{-1}$).

FIG. 3 depicts the selectivity of sensor 1 for $Hg^{2+}$ over other cations at pH 7. Sensor 1 shows a 1.5 fold fluorescence increase at pH 7 upon addition of $Hg^{2+}$. This increase is selective for $Hg^{2+}$. Conditions: 50 mM PIPES, 100 mM KCl, pH 7, 1 μM probe (3 mL) and cation stock solutions are 10 mM (NaCl=100 mM). Fluorescence spectrum of probe is taken with excitation provided at 500 nm. An aliquot (20 uL) of cation solution is added and the fluorescence spectrum is taken. After, an aliquot (20 uL) of 10 mM $Hg^{2+}$ is added and the spectrum is taken. The y-axis is the ratio of fluorescence for the cation-containing solution relative to the free probe.

FIG. 4 depicts the selectivity of sensor 1 for $Hg^{2+}$ over other cations at pH 11. Sensor 1 shows a 5 fold fluorescence increase at pH 11 upon addition of $Hg^{2+}$. This increase is selective for $Hg^{2+}$. Conditions: 50 mM CABS, 100 mM KCl, pH 11, 1 μM probe (3 mL) and cation stock solutions are 10 mM (NaCl=100 mM). Fluorescence spectrum of probe is taken with excitation provided at 500 nm. An aliquot (20 uL) of cation solution is added and the fluorescence spectrum is taken. After, an aliquot (20 uL) of 10 mM $Hg^{2+}$ is added and the spectrum is taken. The y-axis is the ratio of fluorescence for the cation-containing solution relative to the free probe.

FIG. 5 depicts the fluorescence dependence on pH for sensor 1. Conditions: 10 mM KOH, 100 mM KCl, pH adjusted from ~12 to ~3 via addition of 6N, 2N, 1N, 0.5 N, 0.1 N HCl, 1 μM probe (30 mL total volume). The $pK_a$ of 8.2 corresponds to protonation of the tertiary amine. The $pK_a$ of 4.6 corresponds to formation of a non-fluorescent isomer.

FIG. 6 depicts the Job Analysis (to obtain stoichiometry) for sensor 1. Conditions: 10 μM probe, 10 μM $Hg^{2+}$ solution (50 mM PIPES, 100 mM KCl, pH 7). The break (change in slope) occurs at 0.5, indicating a 1:1 Sensor:$Hg^{2+}$ complex in solution.

FIG. 7 depicts the metal binding titration for sensor 1+$Hg^{2+}$ (to obtain stoichiometry) for sensor 1. Conditions: 10 μM probe, aliquots of a 1 mM $Hg^{2+}$ solution added (50 mM CABS, 100 mM KCl, pH 11). The break at 1 equivalent of $Hg^{2+}$ indicates 1:1 stoichiometry in solution.

FIG. 8 depicts the synthesis of $Hg^{2+}$ sensor 2 (Formula 2). This sensor is alternatively referred to throughout the present application as "sensor 2" or "MS2" or "ZS2".

FIG. 9 depicts the selectivity of sensor 2 for $Hg^{2+}$ over other cations at pH 7. Sensor 2 shows a 1.5-fold fluorescence increase at pH 7 upon addition of $Hg^{2+}$. The increase is selective for $Hg^{2+}$. Conditions: 50 mM PIPES, 100 mM KCl, pH 7, 1 μM probe (3 mL) and cation stock solutions are 10 mM (NaCl=100 mM). Fluorescence spectrum of probe is taken with excitation provided at 500 nm. An aliquot (20 uL) of cation solution is added and the fluorescence spectrum is taken. After, an aliquot (20 uL) of 10 mM $Hg^{2+}$ is added and the spectrum is taken. The y-axis is the ratio of fluorescence for the cation-containing solution relative to the free probe.

FIG. 10 depicts the selectivity of sensor 2 for $Hg^{2+}$ over other cations at pH 11. Sensor 2 shows a 6-fold fluorescence increase at pH 11 upon addition of $Hg^{2+}$. This increase is selective for $Hg^{2+}$. Conditions: 50 mM CABS, 100 mM KCl, pH 11, 1 μM probe (3 mL) and cation stock solutions are 10 mM (NaCl=100 mM). Fluorescence spectrum of probe is taken with excitation provided at 500 nm. An aliquot (20 uL) of cation solution is added and the fluorescence spectrum is taken. After, an aliquot (20 uL) of 10 mM $Hg^{2+}$ is added and the spectrum is taken. The y-axis is the ratio of fluorescence for the cation-containing solution relative to the free probe.

FIG. 11 depicts the fluorescence dependence on pH for sensor 2. Conditions: 10 mM KOH, 100 mM KCl, pH adjusted from ~12 to ~3 via addition of 6N, 2N, 1N, 0.5 N, 0.1 N HCl, 1 μM probe (30 mL total volume). The $pK_a$ of 8.0 corresponds to protonation of the tertiary amine. The $pK_a$ of 4.7 corresponds to formation of a non-fluorescent isomer.

FIG. 12 depicts the Job Analysis (to obtain stoichiometry) for sensor 2. Conditions: 10 μM probe, 10 μM $Hg^{2+}$ solution (50 mM PIPES, 100 mM KCl, pH 7). The break (change in slope) occurs at 0.5, indicating a 1:1 Sensor:$Hg^{2+}$ complex in solution.

FIG. 13 depicts the synthesis of $Hg^{2+}$ sensor 3 (Formula 3). This sensor is alternatively referred to throughout the present application as "sensor 3" or "MS3" or "ZS3".

FIG. 14 depicts the fluorescence response of sensor 3 to $Hg^{2+}$. Conditions: 1 mM probe, 0-3 equivalents $Hg^{2+}$ added, (50 mM PIPES, 100 mM KCl, pH 7). The fluorescence spectrum shows an ~7-fold increase in integrated emission upon addition of $Hg^{2+}$ at pH 7 and ~11% increase in integrated emission in the presence of 2 ppb of $Hg^{2+}$ (2 ppb is the EPA limit for inorganic $Hg^{2+}$ in drinking water). Quantum yield and epslion sensor 3 (pH 7): $\Phi_{free}$=0.04 ($\epsilon$=61,400 $M^{-1}$ $cm^{-1}$); $\Phi Hg(II)$=0.11 ($\epsilon$=73,200 $M^{-1}$ $cm^{-1}$). $EC_{50}$=410 nM (500 nM probe; $EC_{50}$=the concentration of $Hg^{2+}$ required to achieve 50% of maximum fluorescence).

FIG. 15 depicts the selectivity of sensor 3 for $Hg^{2+}$ over other cations at pH 7. Sensor 1 shows a ~2.5-fold fluorescence increase at pH 7 upon addition of $Hg^{2+}$. This increase is selective for $Hg^{2+}$. Conditions: 50 mM PIPES, 100 mM KCl, pH 11, 1 μM probe (3 mL) and cation stock solutions are 10 mM (NaCl=100 mM). Fluorescence spectrum of probe is taken with excitation provided at 500 nm. An aliquot (20 uL) of cation solution is added and the fluorescence spectrum is taken. After, an aliquot (20 uL) of 10 mM $Hg^{2+}$ is added and the spectrum is taken. The y-axis is the ratio of fluorescence for the cation-containing solution relative to the free probe.

FIG. 16 depicts the fluorescence dependence on pH for sensor 3. Conditions: 10 mM KOH, 100 mM KCl; pH adjusted from ~12 to ~3 via addition of 6N, 2N, 1N, 0.5 N, 0.1 N HCl, 1 μM probe (30 mL total volume). The $pK_a$ of 7.1 corresponds to protonation of the aniline nitrogen atom. The $pK_a$ of 4.8 corresponds to formation of a non-fluorescent isomer.

FIG. 17 depicts the metal binding titration for sensor 3+$Hg^{2+}$ (to obtain stoichiometry) for sensor 3. Conditions: 10 μM probe, aliquots of a 1 mM $Hg^{2+}$ solution added (50 mM PIPES, 100 mM KCl, pH 7). The break at 1 equivalent of $Hg^{2+}$ indicates 1:1 stoichiometry in solution.

FIG. 18 depicts the reversibility of $Hg^{2+}$ binding to sensor 3 upon addition of TPEN with excitation at 500 nm. Circles:

free sensor 1, [sensor 1]=1 µM; squares: fluorescence increase upon addition of 1 equiv HG9II); diamonds: decrease in fluorescence resulting from addition of 1 equiv TPEN. Inset: normalized integrated emission versus cycle number showing the restoration and decrease of fluorescence upon addition of 1 equiv $Hg^{2+}$ and 1 equiv TPEN, respectively, over the course of five cycles.

FIG. 19 depicts the structure of $Hg^{2+}$ sensor 4 (Formula 4). The crude reaction mixture from the $Hg^{2+}$ sensor 4 synthesis shows a positive fluorescence response upon addition of $Hg^{2+}$ in the presence of chloride ion. This sensor is alternatively referred to throughout the present application as "sensor 4" or "MS4" or "ZS4".

FIG. 20 depicts the synthesis of $Hg^{2+}$ sensor 5 (Formula 5). This sensor is alternatively referred to throughout the present application as "sensor 5" or "MS5" or "ZS5". The disulfide bond in this sensor must be reduced in order to achieved metal ion coordination.

FIG. 21 depicts the synthesis of $Hg^{2+}$ sensor 6 (Formula 6). This sensor is alternatively referred to throughout the present application as "sensor 6" or "MS6" or "ZS6".

FIG. 22 depicts the response of $Hg^{2+}$ sensor 6 to $Hg^{2+}$. MS6 exhibits a fluorescence decrease upon $Hg^{2+}$ coordination.

Figure 1:
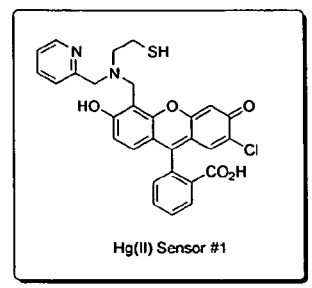
Figure 1:
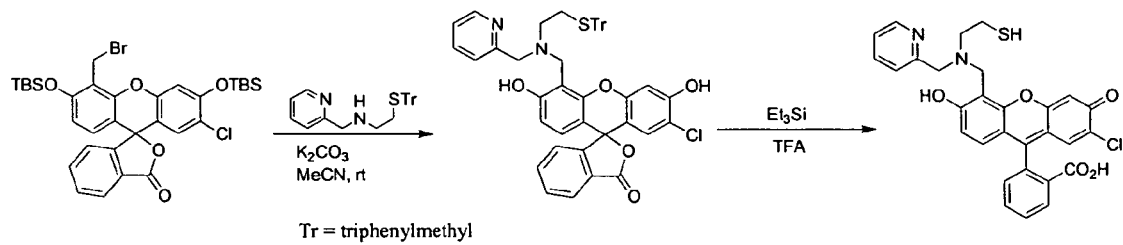

FIG. 23 depicts the synthesis of $Hg^{2+}$ sensor 7 (Formula 7) and certain of its properties. This sensor is alternatively referred to throughout the present application as "sensor 7" or "MS7" or "ZS7". MS7 exhibits a fluorescence decrease upon $Hg^{2+}$ coordination.

FIG. 24 depicts the synthesis of $Hg^{2+}$ sensor 8 (Formula 8). This sensor is alternatively referred to throughout the present application as "sensor 8" or "MS8" or "ZS8".

5. DETAILED DESCRIPTION OF THE INVENTION 5.1. Definitions

For convenience, before further description of the present invention, certain terms employed in the specification, examples and appended claims are collected here. These definitions should be read in light of the remainder of the disclosure and understood as by a person of skill in the art.

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. A Lewis base, when coordinated to a metal ion, is often referred to as a ligand. Further description of ligands relevant to the present invention is presented below.

The term "ligand" is art-recognized and refers to a species that interacts in some fashion with another species. In one example, a ligand may be a Lewis base that is capable of forming a coordinate bond with a Lewis acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The terms "Lewis acid" and "Lewis acidic" are art-recognized and refer to chemical moieties which can accept a pair of electrons from a Lewis base as defined above.

The term "chelating agent" is art-recognized and refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent form coordinate bonds with a single metal ion; however, in certain examples, a chelating agent may form coordinate bonds with more than one metal ion, with a variety of binding modes being possible.

The term "coordination" is art-recognized and refers to an interaction in which one multi-electron pair donor coordinatively bonds (is "coordinated") to one metal ion.

The terms "coordinate bond" or "coordination bond" are art-recognized and refer to an interaction between an electron pair donor and a coordination site on a metal ion leading to an attractive force between the electron pair donor and the metal ion. The use of these terms is not intended to be limiting, in so much as certain coordinate bonds may also be classified as having more or less covalent character (if not entirely covalent character) depending on the nature of the metal ion and the electron pair donor.

The term "coordination site" is art-recognized and refers to a point on a metal ion that can accept an electron pair donated, for example, by a liquid or chelating agent.

The term "free coordination site" is art-recognized and refers to a coordination site on a metal ion that is vacant or occupied by a species that is weakly donating. Such species is readily displaced by another species, such as a Lewis base.

The term "coordination number" is art-recognized and refers to the number of coordination sites on a metal ion that are available for accepting an electron pair.

The term "coordination geometry" is art-recognized and refers to the manner in which coordination sites and free coordination sites are spatially arranged around a metal ion. Some examples of coordination geometry include octahedral, square planar, trigonal, trigonal biplanar and others known to those of skill in the art.

The term "complex" is art-recognized and means a compound formed by the union of one or more electron-rich and electron-poor molecules or atoms capable of independent existence with one or more electronically poor molecules or atoms, each of which is also capable of independent existence. A "coordination complex" is one type of a complex, in which there is a coordinate bond between a metal ion and an electron pair donor. A metal ion complex is a coordination complex in which the metal ion is a metal ion. In general, the terms "compound," "composition," "agent" and the like discussed herein include complexes, coordination complexes and metal ion complexes. As a general matter, the teachings of *Advanced Inorganic Chemistry* by Cotton and Wilkinson are referenced as supplementing the definitions herein in regard to coordination complexes and related matters.

In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands.

If a coordination complex is charged, in that the metal ion and any Lewis bases in the aggregate are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetraflurorborate, hexafluorophosphate, and monocarboxylates, and dianions such as sulfate. In some cases, coordination complexes themselves may serve as counterions to another coordination complex.

The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors including theoretical considerations such as kinetic versus thermodynamic effects, as well as the actual synthetic procedures utilized to make the coordination complex, such as the extent of reaction, acidity, concentration of chloride. These considerations are applicable to other counterions as well.

Additionally, a coordination complex may be solvated. Solvation refers to molecules, usually of solvent and often water, that associate with the coordination complex in the solid state. Again, as for counterions, such solvation molecules may or may not be considered part of the coordination complex depending on how the term coordination complex is used.

The term "synthetic" is art-recognized and refers to production by in vitro chemical or enzymatic synthesis.

The term "meso compound" is art-recognized and means a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular Formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

"Small molecule" is an art-recognized term. In certain embodiments, this term refers to a molecule which has a molecular weight of less than about 2000 amu, or less than about 1000 amu, and even less than about 500 amu.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfonyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfonyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN, and the like.

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and includes an aromatic or non-aromatic ring in which each atom of the ring is carbon. The following art-recognized terms have the following meanings: "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and include both unsubstituted and substituted amines, e.g., a moiety that may be represented by the general formulas:

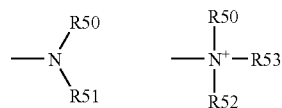

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

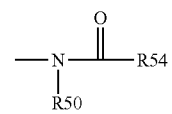

wherein R50 is as defined above, and R54 represents a hydrogen, an alkyl, an alkenyl or —(CH$_2$)$_m$—R61, where m and R61 are as defined above.

The term "amido" is art-recognized as an amino-substituted carbonyl and includes a moiety that may be represented by the general formula:

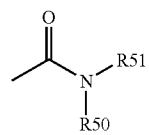

wherein R50 and R51 are as defined above. Certain embodiments of the amide in the present invention will not include imides which may be unstable.

The term "alkylthio" is art-recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art-recognized and includes such moieties as may be represented by the general formulas:

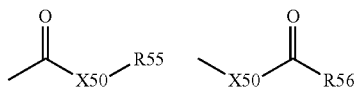

wherein X50 is a bond or represents an oxygen or a sulfur, and R55 represents a hydrogen, an alkyl, an alkenyl, —(CH$_2$)$_m$—R61, or a pharmaceutically acceptable salt. R56 represents a hydrogen, an alkyl, an alkenyl or —(CH$_2$)$_m$—R61, where m and R61 are defined above. Where X50 is an oxygen and R55 or R56 is not hydrogen, the Formula represents an "ester". Where X50 is an oxygen, and R55 is as defined above, the moiety is referred to herein as a carboxyl group, and particularly when R55 is a hydrogen, the Formula represents a "carboxylic acid". Where X50 is an oxygen, and R56 is hydrogen, the Formula represents a "formate". In general, where the oxygen atom of the above Formula is replaced by sulfur, the Formula represents a "thiocarbonyl" group. Where X50 is a sulfur and R55 or R56 is not hydrogen, the Formula represents a "thioester." Where X50 is a sulfur and R55 is hydrogen, the Formula represents a "thiocarboxylic acid." Where X50 is a sulfur and R56 is hydrogen, the Formula represents a "thioformate." On the other hand, where X50 is a bond, and R55 is not hydrogen, the above Formula represents a "ketone" group. Where X50 is a bond, and R55 is hydrogen, the above Formula represents an "aldehyde" group.

The terms "alkoxyl" or "alkoxy" are art-recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art-recognized and includes a moiety that may be represented by the general formula:

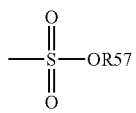

in which R57 is an electron pair, hydrogen, alkyl, cycloalkyl, or aryl.

The term "sulfate" is art-recognized and includes a moiety that may be represented by the general formula:

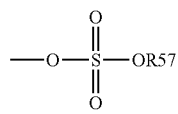

in which R57 is as defined above.

The term "sulfonamido" is art-recognized and includes a moiety that may be represented by the general formula:

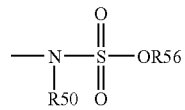

in which R50 and R56 are as defined above.

The term "sulfonyl" is art-recognized and includes a moiety that may be represented by the general formula:

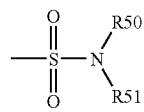

in which R50 and R51 are as defined above.

The term "sulfonyl" is art-recognized and includes a moiety that may be represented by the general formula:

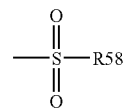

in which R58 is one of the following: hydrogen, alkyl, alkenyl, alkynyl, cycloalkyl, heterocyclyl, aryl or heteroaryl.

The term "sulfoxido" is art-recognized and includes a moiety that may be represented by the general formula:

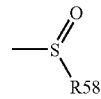

in which R58 is defined above.

The term "phosphoryl" is art-recognized and includes moieties represented by the general formula:

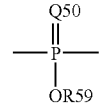

wherein Q50 represents S or O, and R59 represents hydrogen, a lower alkyl or an aryl. When used to substitute, e.g., an alkyl, the phosphoryl group of the phosphorylalkyl may be represented by the general formulas:

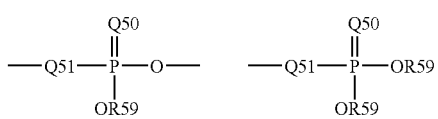

wherein Q50 and R59, each independently, are defined above, and Q51 represents O, S or N. When Q50 is S, the phosphoryl moiety is a "phosphorothioate".

The term "phosphoramidite" is art-recognized and includes moieties represented by the general formulas:

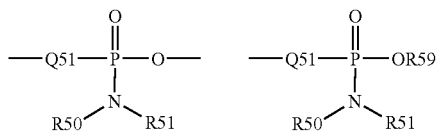

wherein Q51, R50, R51 and R59 are as defined above.

The term "phosphoramidite" is art-recognized and includes moieties represented by the general formulas:

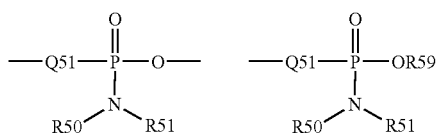

wherein Q51, R50, R51 and R59 are as defined above.

The term "phosphonamidite" is art-recognized and includes moieties represented by the general formulas:

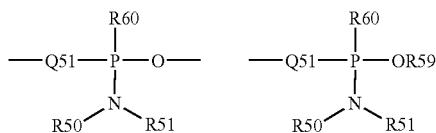

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

The term "selenoalkyl" is art-recognized and includes an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art-recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations.*

Certain compositions of the present invention may exist in particular geometric or stereoisomeric forms. In addition, certain compositions of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that the terms "substitution" and "substituted with" are art-recognized and include the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986-87, inside cover. The term "hydrocarbon" is art-recognized and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "protecting group" is art-recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., *Protective Groups in Organic Synthesis* $2^{nd}$ ed., Wiley, N.Y., (1991).

The phrase "hydroxyl-protecting group" is art-recognized and includes those groups intended to protect a hydroxyl group against undesirable reactions during synthetic procedures and includes, for example, benzyl or other suitable esters or ethers groups known in the art.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251-59, McGraw Hill Book Company, New York, (1977). The Hammett constant values are generally negative for electron donating groups ($\sigma(P)=-0.66$ for $NH_2$) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —$CH(NH_2)COOH$ portion, as defined by Kopple, *Peptides and Amino Acids* 2, 33 (W. A. Benjamin Inc., New York and Amsterdam, 1966); examples of such side chains of the common amino acids are —$CH_2CH_2SCH_3$ (the side chain of methionine), —$CH_2CH(CH_3)_2$ (the side chain of leucine) or —H (the side chain of glycine).

The term "amino acid" is intended to embrace all compounds, whether natural or synthetic, which include both an amino functionality and an acid functionality, including amino acid analogs and derivatives. In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject compounds may include an amino acid analog such as, for example, cyanoalanine, canavanine, djenkolic acid, norleucine, 3-phosphoserine, homoserine, dihydroxyphenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers may be obtained in substantially pure form by classical separation techniques and by sterically controlled synthesis. For the purposes of this application, unless expressly noted to the contrary, a named amino acid shall be construed to include both the (D) or (L) stereoisomers. In the majority of cases, D- and L-amino acids have R- and S-absolute configurations, respectively.

The names of the natural amino acids are abbreviated herein in accordance with the recommendations of IUPAC-IUB.

The term "antibody" is art-recognized and intended to include whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

The terms "human monoclonal antibodies" and "humanized" murine antibodies, are art-recognized and refer to murine monoclonal antibodies "humanized" by genetically recombining the nucleotide sequence encoding the murine Fv region (i.e., containing the antigen binding site) or the complementarity-determining regions thereof with the nucleotide sequence encoding at least a human constant domain region and an Fc region, e.g., in a manner similar to that disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

The term "target" is art-recognized and means a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). Certain target infectious organisms include those that are drug resistant (e.g., *Enterobacteriaceae, Enterococcus, Haemophilus influenza, Mycobacterium tuberculosis, Neisseria gonorrhoeae, Plasmodium falciparum, Pseudomonas aeruginosa, Shigella dysenteriae, Staphylococcus aureus, Streptococcus pneumoniae*). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

The term "target cell", which is art-recognized, and which cells may serve as the target for methods of the present invention, include prokaryotes and eukaryotes, including yeasts, plant cells and animal cells. Target cells may include, for example, the cells lining the alimentary canal, such as the oral and pharyngeal mucosa, cells forming the villi of the small intestine, cells lining the large intestine, cells lining the respiratory system (nasal passages/lungs) of an animal (which may be contacted by inhalation of the subject invention), dermal/epidermal cells, cells of the vagina and rectum, cells of internal organs including cells of the placenta and the so-called blood/brain barrier, etc.

The term "targeting moiety" is art-recognized and refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

A "patient," "subject", or "host" to be treated by the subject method is art-recognized, and means either a human or non-human animal.

The term "bioavailable" is art-recognized and means that a compound the subject invention is in a form that allows for it, or a portion of the amount administered, to be absorbed by, incorporated to, or otherwise physiologically available to a subject or patient to whom it is administered.

The term "treating" is an art-recognized term which includes curing as well as ameliorating at least one symptom of any condition or disease. Diagnostic applications are also examples of "treating".

The phrase "pharmaceutically acceptable" is art-recognized. In certain embodiments, the term includes compositions, fluorescein-based ligands and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical Formulations.

The term "pharmaceutically acceptable salts" is art-recognized, and includes relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.*, 66:1-19 (1977).

The phrases "systemic administration," "administered systemically," "peripheral administration" and "administered peripherally" are art-recognized, and include the administration of a subject supplement, composition, therapeutic or other material other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that produces some desired effect at a reasonable benefit/risk ratio applicable to any medical treatment. In certain embodiments, the term refers to that amount necessary or sufficient for diagnostic use of the subject compositions. One of ordinary skill in the art may empirically determine the effective amount of a particular compound without necessitating undue experimentation.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index"

is an art-recognized term which refers to the therapeutic index of a drug, defined as $LD_{50}/ED_{50}$.

Contemplated equivalents of the fluorescein-based ligands, scaffold molecules and other compositions described herein include such materials which otherwise correspond thereto, and which have the same general properties thereof, wherein one or more simple variations of substituents are made which do not adversely affect the efficacy of such molecule to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

5.2. General Description of Fluorescein-based Ligands

A variety of fluorescein-based ligands, and methods of using and making the same, are contemplated by the present invention. In certain embodiments, the subject ligands form coordination complexes with a variety of metal ions, with a concomitant change in the fluorescent properties of the resulting metal complex as compared to the uncomplexed ligand. In certain embodiment, such ligands may be used to assay for metal ions including as non-limiting examples heavy metal ions. A variety of methods of preparing such ligands and the coordination complexes, of assaying for the binding activity of such ligands, and of using such compositions are also taught by the subject invention. A number of different ligands and metal ions are contemplated for the subject coordination complexes, as set out in more detail below.

The carbon positions at which substitutions are able to be made on a fluorescein molecule are numbered according to the system shown in the figure below. This system is known to those of skill in the art, and will be used to refer to various atoms of the fluorescein molecules in the description, exemplification, and claims below.

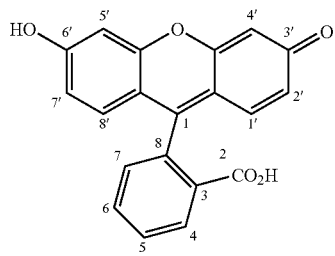

By way of a general, non-limiting description, fluorescein exists in three isomeric forms that are favored under different conditions shown below. The free acid is favorable under aqueous conditions and in polar solvents, the lactone is present in non-polar media, and the zwitterion is an isolable intermediate. Addition of acetate, benzoate or silyl protecting groups to the phenols imposes the lactone isomer. In a stable lactone form, fluoresceins may be purified by standard experimental techniques and identified by NMR and IR spectroscopy. In general, it is the deprotonated free acid form of fluorescein that accounts for the compounds' strong fluorescence.

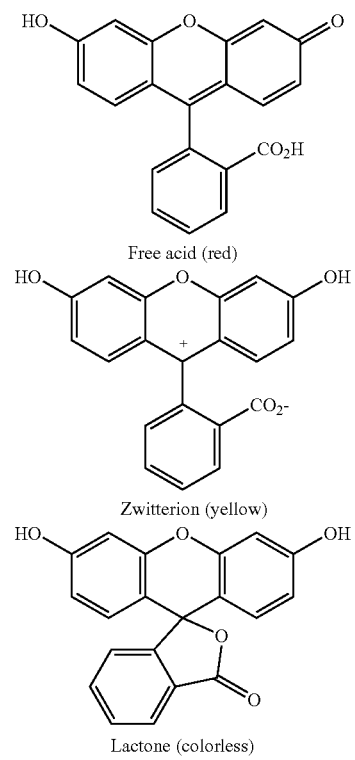

5.3. Exemplary Fluorescein-Based Ligands

In part, the subject invention is directed to the fluorescein-based ligands represented by Formula 9A:

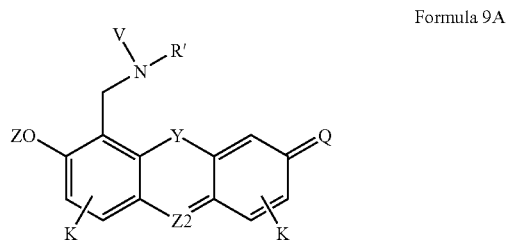

Formula 9A wherein Z is hydrogen or any hydroxyl-protecting group known in the art; Q is O, S, Se; K is optionally one or more substituents of the indicated aromatic ring that do not materially alter the fluorescence of the ligand as described below; V is a Lewis base; R' is H, alkyl or V, wherein at least one V comprises at least one sulfur-containing moiety capable of forming one or more coordination bonds with a metal ion; Y is O, S, Se, NR, or C(CH3)3, wherein R is an alkyl and R and the methyl groups of $C(CH_3)_2$ are optionally substituted; and Z2 is N, $HOOCCH_2CH_2C$—, HOOC—CH=CH—C—, (2-carboxyphenyl)-C—, (2-sulfophenyl)-C—, (2-carboxy-3,4,5,6-tetrachlorophenyl)-C—, (2-carboxy-4-nitrophenyl)-C—, (2-carboxy-5-nitrophenyl)-C—, (2-carboxy-4-aminophenyl)-C—, (2-carboxy-5-aminophenyl)-C—, (2,4-dicarboxyphenyl)-C—, (2,5-dicarboxylphenyl)-C—, (2,4,5-tricarboxyphenyl)-C—, and other substituted (2-carboxyphenyl)-C-moieties. If Q is —OZ, whereupon a different tautomer is obtained, Z2 varies accordingly.

In part, Formula 9A, with exemplary substitution becomes:

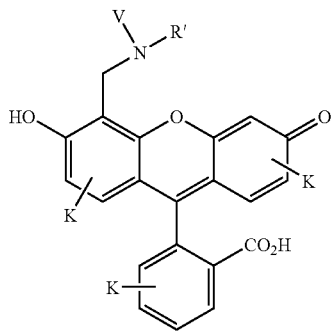

Formula 9B

In general, K is a chemical moiety that does not preclude using the resulting fluorescein-based ligand for detection of an analyte of interest. K may be any one or more substituents at any of the aromatic ring carbon positions. In general, the 2' and 7' positions of the fluorescein core is more likely to be substituted, whereas the 1' and 8' positions are less likely to be substituted.

Alternatively, in certain other preferred embodiments, K is not a electron-withdrawing group in the 2' position of the fluorescein-based ligands. An example of such an electron-withdrawing group is any halogen, and more specifically, chlorine. The absence of such an electron-withdrawing K moiety in such position(s) may affect the fluorescent properties of the subject compositions (whether coordinated to a metal ion or not), as well as the methods by which such compositions may be prepared.

In certain embodiments each K, independently, may be a linear or branched alkyl, alkenyl, linear or branched aminoalkyl, linear or branched acylamino, linear or branched acyloxy, linear or branched alkoxycarbonyl, linear or branched alkoxy, linear or branched alkylaryl, linear or branched hyrdoxyalkyl, linear or branched thioalkyl, acyl, amino, hydroxy, thio, aryloxy, arylalkoxy, hydrogen, alkynyl, halogen, cyano, sulfhydryl, carbamoyl, nitro, trifluoromethyl, amino, thio, lower alkoxy, lower alkylthio, lower alkylamino, nitro, phenoxy, benzyloxy, hydrogen, amine, hydroxyl, alkoxyl, carbonyl, acyl, formyl, sulfonyl and the like.

The identity of K will affect the fluorescence properties of the resulting compound, as known to one of skill in the art. A variety of mechanisms may explain the affect of K on fluorescence, often by quenching, including, for example, double bond torsion, low energy n□* levels, "heavy" atoms, weak bonds, photoinduced electron transfer (PET) and electronic energy transfer (EET). For example, any K substituents having unpaired electrons at the atom directly attached to the aromatic ring, such as an amine or phenol derivative, are expected to result in quenching of the fluorescence of the uncomplexed ligand. If, however, upon complexation with a metal ion that atom forms a coordinate bond, then quenching through that mechanism should cease, which would give a greater signal for that particular compound upon binding to the analyte of interest.

In preferred embodiments, K is an electron-withdrawing group that is not a Lewis base, such as the halogens and trifluoromethyl, and in particularly preferred embodiments, K is —F or —Cl.

In certain embodiments, V is capable of forming at least a bidentate chelating agent consisting of a sulfur atom of V donating an electron pair and the oxygen atom of the adjacent hydroxyl group(s) of the fluorescein ring structure. Alternatively, V itself includes two or more atoms that serve as Lewis bases and are capable of forming bidentate, tridentate, tetradentate or greater chelating agents by themselves or in conjunction with the oxygen atoms of the hydroxyl substituents of the fluorescein structure. In certain embodiments, the atoms that serve to donate electrons for V are nitrogen, oxygen, sulfur or phosphorus.

In general, V contains a Lewis base fragment comprising at least one sulfur-containing moiety that may also further encompass numerous chemical moieties having a variety of structural, chemical and other characteristics capable of forming coordination bonds with a metal ion. The types of functional groups capable of forming coordinate complexes with metal ions are too numerous to categorize here, and are known to those of skill in the art. For example, such moieties will generally include functional groups capable of interaction with a metal center, e.g., heteroatoms such as nitrogen, oxygen, sulfur, and phosphorus.

Metal cations are almost always Lewis acidic and are therefore able to bind various moieties that may serve as Lewis bases. In general, a moiety serving as a Lewis base will be a strongly acidic group, e.g., with a pKa less than about 7, and more preferably less than 5, which may produce a conjugate base that, under the appropriate conditions, is a strong enough Lewis base to donate an electron pair to a metal ion to form a coordinate bond. The degree of this Lewis acid-to-Lewis base interaction is a function not only of the particular metal ion, but also of the coordinating moiety itself, because the latter may vary in the degree of basicity as well as in size and steric accessibility.

Exemplary Lewis basic moieties comprising sulfur-containing moieties which may be included in V include (assuming appropriate modification of them to allow for their incorporation into V and the subject fluorescein-based ligands): thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfonyls and sulfinyls.

Such Lewis basic moieties may comprise in addition to a sulfur-containing moiety: amines (primary, secondary, and tertiary) and aromatic amines, amino groups, amido groups, nitro groups, nitroso groups, amino alcohols, nitriles, imino groups, isonitriles, cyanates, isocyanates, phosphates, phosphonates, phosphites, phosphines, phosphine oxides, phosphorothioates, phosphoramidates, phosphonamidites, hydroxyls, carbonyls (e.g., carboxyl, ester and formyl groups), aldehydes, ketones, ethers, and carbamoyl groups.

Illustrative of suitable V include those chemical moieties containing at least one Lewis basic sulfur atom or a combination of such sulfur atoms and at least one other nitrogen, phosphorous or oxygen atom. The carbon atoms of such moiety may be part of an aliphatic, cycloaliphatic or aromatic moiety. In addition to the organic Lewis base functionality, such moieties may also contain other atoms and/or groups as substituents, such as alkyl, aryl and halogen substituents.

Further examples of Lewis base functionalities suitable for use in V include the following chemical moieties (assuming appropriate modification of them to allow for their incorporation into V and the subject fluorescein-based ligands): amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolamine, N-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like; and heterocyclic compounds, including pyridine and the like.

Other suitable structural moieties that may be included in V include the following Lewis base functionalities: arsine, stilbines, thioethers, selenoethers, teluroethers, thioketones, imines, phosphinimine, pyridines, pyrazoles, imidazoles, furans, oxazoles, oxazolines, thiophenes, thiazoles, isoxazoles, isothrazoles, amides, alkoxy, aryoxy, selenol, tellurol, siloxy, pyrazoylborates, carboxylate, acyl, amidates, triflates, thiocarboxylate and the like.

Other suitable ligand fragments for use in V include structural moieties that are bidentate ligands, including diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

Still other suitable fragments for use in V include ligand fragments that are tridentate ligands, including 2,5-diiminopyridyl ligands, tripyridyl moieties, triimidazoyl moieties, tris pyrazoyl moieties, and combinations of the above ligands.

Other suitable ligand fragments may consist of amino acids or be formed of oligopeptides and the like.

Because the Lewis basic groups function as the coordination site or sites for the metal cation, in certain embodiments, it may be preferable that the deformability of the electron shells of the Lewis basic groups and the metal cations be approximately similar. Such a relationship often results in a more stable coordination bond. Many heavy metal ions are "soft" Lewis acids, which means that their affinity for soft donor atoms such as phosphorus and sulfur are considerably higher than for hard donor atoms such as nitrogen and oxygen. Examples of heavy metal ions are $Hg^{2+}$, $Pb^{2+}$, $Cd^{2+}$, $Cu^{2+}$, $Ag+$, $Au3+$, $Pt4+$, and $Tl+$. Thus, sulfur and phosphorous containing moieties may be desirable as the Lewis basic groups when the metal cation is a heavy metal. Some examples include the oligopeptides such as glutathione and cysteine, mercapto ethanol amine, dithiothreitol, amines and peptides containing sulfur and the like. Alternatively, for those applications in which a less stable coordination bond is desired, it may be desirable that the deformability be dissimilar. Nitrogen containing groups may be employed as the Lewis basic groups when smaller metal ions are the metal.

In part, Formula 9A, with exemplary substitution becomes:

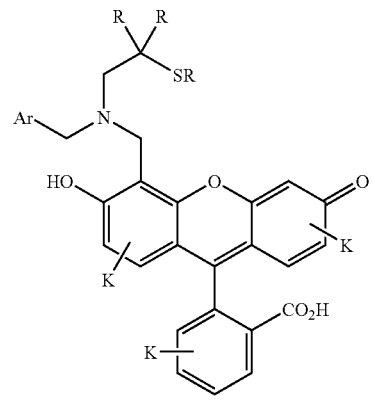

9C wherein, Ar stands for an aryl ring; and R, independently for each occurrence, is H, alkyl, or aryl.

In part, Formula 9A, with exemplary substitution becomes:

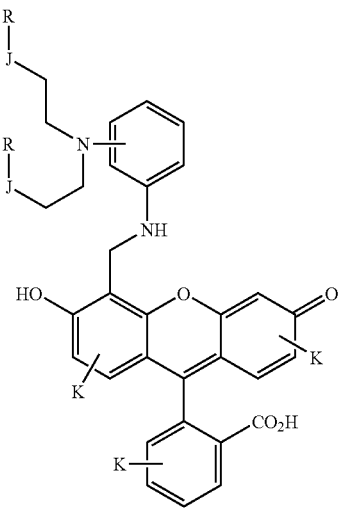

9D wherein, J is a heteroatom provided that at least one J is S; and R is H, alkyl, or aryl. The number of Rs present is enough to satisfy the valency of J.

Additional substitution of Formula 9A yields:

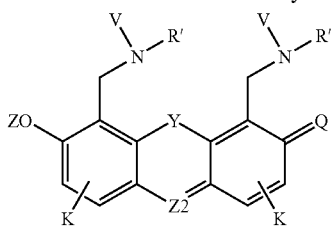

9E wherein only one V need contain a sulfur moiety.

Examples of a fluorescein-based ligand are present in Formulas 10, 11, and 12 below, in which V by itself or in conjunction with another V forms a tridentate ligand, and in conjunction with the adjacent hydroxyls a tetradentate ligand:

Formula 10

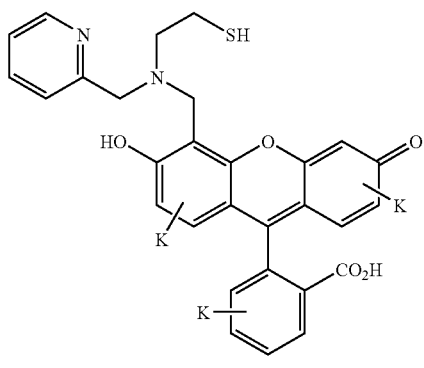

(Sensor 1)

Formula 11

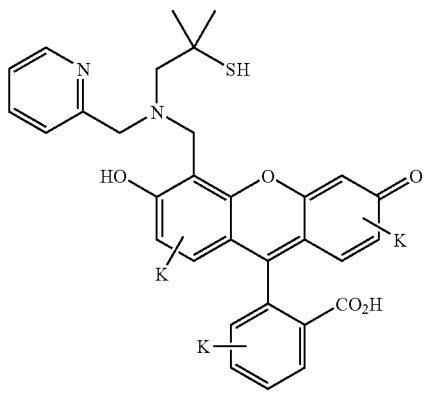

(Sensor 2)

Formula 12

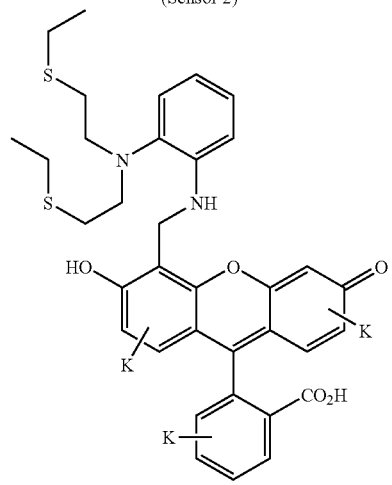

(Sensor 3)

In certain embodiments of the compound of Formulas 10, 11, and 12, K is a halogen, preferably a chloride, at the 7' position of the fluorescein structure.

Upon addition to an aqueous solution containing $Hg^{2+}$ at about pH 7.0, the fluorescence of the fluorescein-based ligands of Formulas 10, 11, and 12 may increase by at least about 5%, at least about 7%, about 10%, about 50%, about 60%, about 70%, about 80%, about 90%, about 95%, about 97%, about 98%, about 99%, about 100%, about 150%, about 200%, about 300% or even 500% or more.

Other examples of a fluorescein-based ligand are present in Formulas 13, 14, and 15 below:

Formula 13

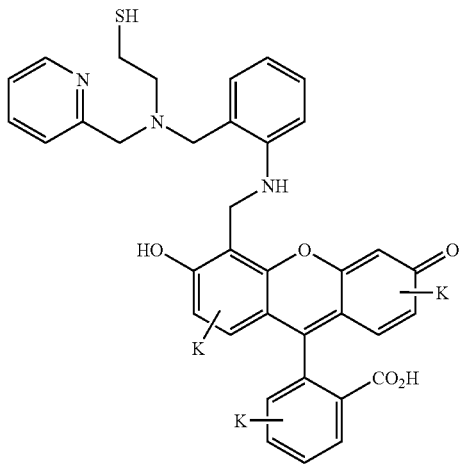

(Sensor 4)

Formula 14

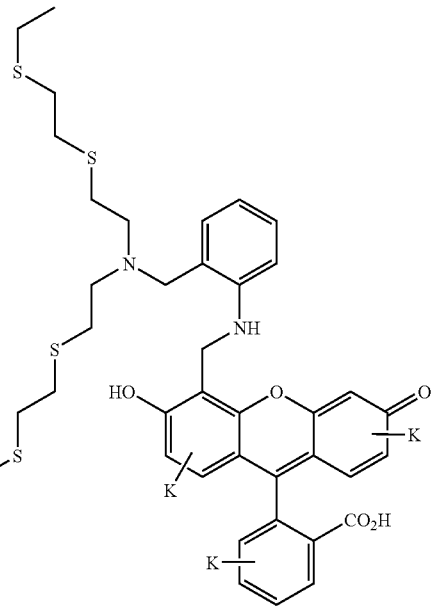

(Sensor 6)

-continued

Formula 15

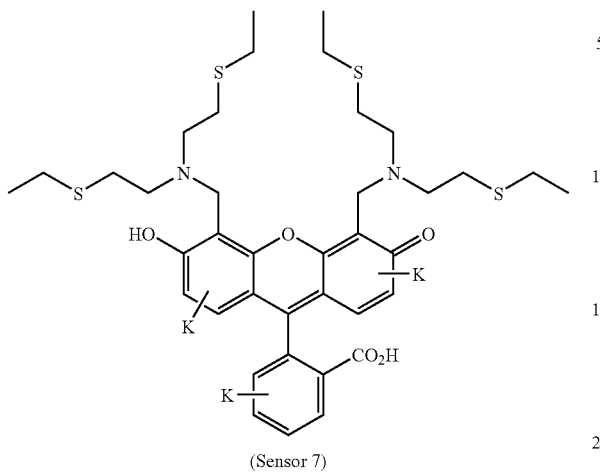

(Sensor 7)

In certain embodiments of the compound of Formulas 13, 14, and 15, K is a halogen, preferably a chloride, at the 7' position of the fluorescein structure.

Upon addition to an aqueous solution containing $Hg^{2+}$ at about pH 7.0, the fluorescence of the fluorescein-based ligands of Formula 13 may increase by at least about 5%, at least about 7%, about 10%, about 50%, about 60%, about 70%, about 80%, about 90%, about 95%, about 97%, about 98%, about 99%, about 100%, about 150%, about 200%, about 300% or even 500% or more.

Upon addition to an aqueous solution containing $Hg^{2+}$ at about pH 7.0, the fluorescence of Formulas 14 and 15 may decrease by at least about 5%, at least about 7%, about 10%, about 50%, about 60%, about 70%, about 80%, about 90%, about 95%, about 97%, about 98%, about 99%, about 100%, about 150%, about 200%, about 300% or even 500% or more.

Yet another example of a fluorescein-based ligand is present in Formula 16 below:

Formula 16

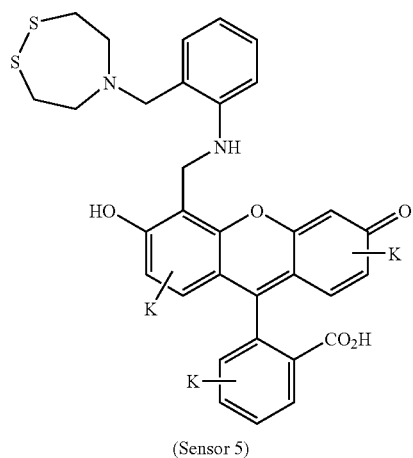

(Sensor 5)

In certain embodiments of the compound of Formula 16, K is a halogen, preferably a chloride, at the 7' position of the fluorescein structure.

Still another example of a fluorescein-based ligand is present in Formula 17 below:

Formula 17

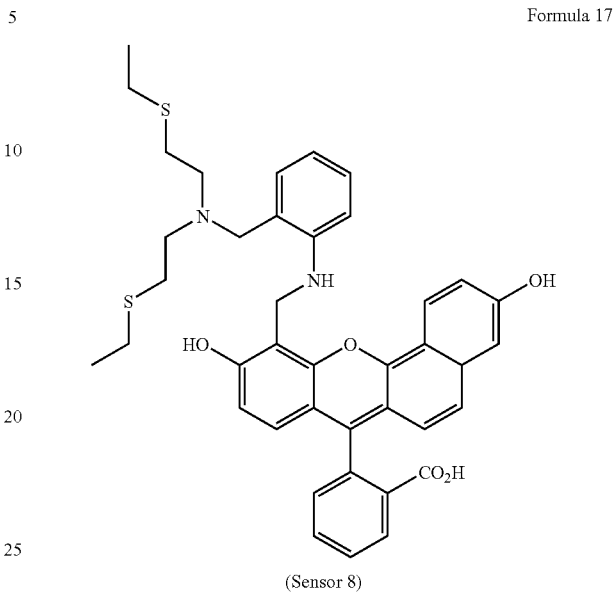

(Sensor 8)

All of these compounds may be prepared by the methods taught herein in conjunction with methods known to those of skill in the art.

5.4. Exemplary Metal Ions

The metal atom that may form a coordination complex with the subject ligands or used in the subject methods may be selected from those that have usually at least three, four, five, six, seven coordination sites or more. In certain embodiments, the subject ligands and methods may be used to coordinate a wide range of metal ions, including light metals (Groups IA and IIA of the Periodic Table), transition metals (Groups IB-VIIIB of the Periodic Table), posttransition metals, metals of the lanthanide series and metals of the actinide series. A non-limiting list of metal ions for which the present invention may be employed (including exemplary oxidation states for them) includes: $Li^+$, $Na^+$, $K^+$, $Mg^+$, $Ca^+$, $Zn^{2+}$, $Cd^{2+}$, $Hg^{2+}$, $Cu^{2+}$, $Pd^{2+}$, $Pt^{2+}$.

In certain embodiments, the metal atom is a heavy metal atom, such as for example, $Hg^{2+}$, $Pb^{2+}$, $Cd^{2+}$, $Cu^{2+}$, Ag+, Au3+, Pt4+, and Tl+.

Concentrations of metal ions are commonly expressed as parts per billion, ppb. A ppb is equivalent to 1 μg per L. By way of example, 2 ppb is the EPA limit for inorganic $Hg^{2+}$ in drinking water.

The design of a fluorescein-based ligand for detecting a particular metal ion will be possible by one of skill in the art, wherein issues such as selectivity, quantum yield, ease of synthesis and the like will be important criteria. By way of example, it has been observed that the fluorescence of ligands complexed to redox active transition metal ions is often quenched, and such quenching is usually attributed to EET with some contribution from the heavy atom effect and PET. Accordingly, to prepare fluorescein-based ligands that will serve as sensors for transition metal ions with unpaired d electrons, it will be necessary to take this effect into account.

5.5. Fluorescence Assays

5.5.1 Instrumentation

Fluorescence of a ligand provided by the present invention may be detected by essentially any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor. Such means for controlling wavelengths are referred to generically as filters and can include diffraction gratings, dichroic mirrors, or filters. Examples of suitable devices include fluorimeters, spectrofluorimeters and fluorescence microscopes. Many such devices are commercially available from companies such as Hitachi, Nikon or Molecular Dynamics. In certain embodiments, the device is coupled to a signal amplifier and a computer for data processing.

5.5.2 General Aspects

In general, assays using fluorescein-based ligands provided by the present invention involve contacting a sample with such a ligand and measuring fluorescence. The presence of a metal ion that interacts with the ligand may alter fluorescence of the ligand in many different ways. Essentially any change in fluorescence caused by the metal may be used to determine the presence of the metal and, optionally the concentration of the metal, in the sample.

The change may take one or more of several forms, including a change in excitation or emission spectra, or a change in the intensity of the fluorescence and/or quantum yield. These changes may be either in the positive or negative direction and may be of a range of magnitudes, which preferably will be detectable as described below.

The excitation spectrum is the wavelengths of light capable of causing the ligand to fluoresce. To determine the excitation spectrum for a ligand in a sample, different wavelengths of light are tested sequentially for their abilities to excite the sample. For each excitation wavelength tested, emitted light is measured. Emitted light may be measured across an interval of wavelengths (for example, from 450 to 700 nm) or emitted light may be measured as a total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by metal in a sample may be used as the basis for determining the presence, and optionally, the concentration of metal in the sample. Alternatively, the emission spectrum may be determined by examining the spectra of emitted light in response to excitation with a particular wavelength (or interval of wavelengths). A profile of emissions at different wavelengths is created and the wavelength at which emission is maximal is called the maximum emission wavelength. Changes in the maximum emission wavelength or the shape of the profile that are caused by the presence of a metal in a sample may be used to determine the presence or concentration of the metal ion in the sample. Changes in excitation or emission spectra may be measured as ratios of two wavelengths. A range of changes are possible, from about a few nms to 5, 10, 15, 25, 50, 75 100 or more nms.

Quantum yield, $\Phi$, may be obtained by comparison of the integrated area of the corrected emission spectrum of the sample with that of a reference solution. A preferred reference solution is a solution of fluorescein in 0.1 N NaOH, quantum efficiency 0.95. The concentration of the reference is adjusted to match the absorbance, Abs, of the test sample. The quantum yields may be calculated using the following equation:

$$\Phi_{sample} = \Phi_{standard} \times \frac{\int emission_{sample}}{\int emission_{standard}} \times \frac{Abs_{standard}}{Abs_{sample}}$$

A change in quantum yield caused by a metal ion may be used as the basis for detecting the presence of the metal in a sample and may optionally be used to determine the concentration of the metal ion. A range of changes are possible in the subject invention. For example, the difference in the quantum yield for a subject fluorescein-based ligand in the presence of a metal ion may be about 10%, 25%, 50%, 75% of the quantum yield of the subject fluorescein-based ligand in the absence of the metal, or it may be 2, 3, 5, 10, 100, 200, 1000, 10000 times greater or more. The same values may be used to describe changes observed in intensity in such the subject assays.

It is expected that some samples will contain compounds that compete for metal-binding with the fluorescent ligand. In such cases, the fluorescence measurement will reflect this competition. In one variation, the fluorescence may be used to determine the presence or concentration of one or more such metal binding compounds in a sample.

5.5.3 In vitro Assays

In one variation, the presence of a metal ion in a sample is detected by contacting the sample with a fluorescein-based ligand that is sensitive to the presence of the metal. The fluorescence of the solution is then determined using one of the above-described devices, preferably a spectrofluorimeter. Optionally, the fluorescence of the solution may be compared against a set of standard solutions containing known quantities of the metal. Comparison to standards may be used to calculate the concentration of the analyte, i.e. the metal ion.

The metal may be essentially any substance described above. The concentration of the metal may change over time and the fluorescent signal may serve to monitor those changes. For example, the particular form of the metal that interacts with the ligand may be produced or consumed by a reaction occurring in the solution, in which case the fluorescence signal may be used to monitor reaction kinetics.

In certain embodiments, the sample is a biological fluid, lysate, homogenate or extract. The sample may also be an environmental sample such as a water sample, soil sample, soil leachate or sediment sample. The sample may be a biochemical reaction mixture containing at least one protein capable of binding to or altering a metal. Samples may have a pH of about 5, 6, 7, 8, 9, 10, 11, 12 or higher.

5.5.4 In vivo Assays

In another variation, the presence of a metal ion in a biological sample may be determined using a fluorescence microscope and the subject fluorescein-based ligands. The biological sample is contacted with the fluorescent sensor and fluorescence is visualized using appropriate magnification, excitation wavelengths and emission wavelengths. In order to observe co-localization of multiple analytes, the sample may be contacted with multiple fluorescent molecules simultaneously. In certain embodiments the multiple fluorescent molecules differ in their emission and/or excitation wavelengths.

Biological samples may include bacterial or eukaryotic cells, tissue samples, lysates, or fluids from a living organism. In certain embodiments, the eukaryotic cells are nerve cells, particularly glutamate neurons. In other embodiments, the eukaryotic cells are neurons with mossy fiber terminals isolated from the hippocampus. Tissue samples are preferably sections of the peripheral or central nervous systems, and in particular, sections of the hippocampus containing mossy fiber terminals. It is also anticipated that the detection of a metal in a cell may include detection of the metal in subcellular or extracellular compartments or organelles. Such subcellular organelles and compartments include: Golgi networks and vesicles, pre-synaptic vesicles, lysosomes, vacuoles, nuclei, chromatin, mitochondria, chloroplasts, endoplasmic reticulum, coated vesicles (including clathrin coated vesicles), caveolae, periplasmic space and extracellular matrices.

5.5.5 Assays using Subject Compounds

The solution or biological sample is contacted with a subject ligand, and fluorescence of the ligand is excited by light with wavelengths ranging from 340 nm to 600 nm. Light emitted by the ligand is detected by detecting light of wavelengths greater than 480 nm. In certain embodiments the excitation wavelengths range from 450 to 510 nm and the detection wavelengths are greater than 535 nm.

6. EXEMPLIFICATION

The present invention now being generally described, it may be more readily understood from the following examples, which are presented herein for illustration only and should not be construed as limiting the invention.

EXAMPLE 1

Reagents. Ethyl acetate (EtOAc) was dried over 3 Å molecular sieves. 1,2-Dichloroethane (DCE) was distilled from calcium hydride under nitrogen and stored over molecular sieves. Acetonitrile was either distilled over $CaH_2$ under nitrogen or was saturated with Ar and dried by passing through an activated $Al_2O_3$ column. 3,9-Dithia-6-azaundecane was synthesized as previously described. All other reagents were used as received.

EXAMPLE 2

Methods. Silica gel-60 (230-400 mesh) was used as the solid phase for flash chromatography and thin layer chromatography (TLC) was performed by using Merck F254 silica gel-60 plates. TLC plates were visualized with UV light or after developing with ninhydrin stain. $^1H$ and $^{13}C$ NMR spectra were obtained either on a Varian 300 MHz or a Varian 500 MHz spectrometer operating at ambient probe temperature, 283 K, and referenced to internal probe standards. IR spectra were recorded by using an Avatar 360 FTIR instrument. Electrospray ionization (ESI) spectroscopy was performed in the MIT Department of Chemistry Instrumentation Facility.

Figure 13:
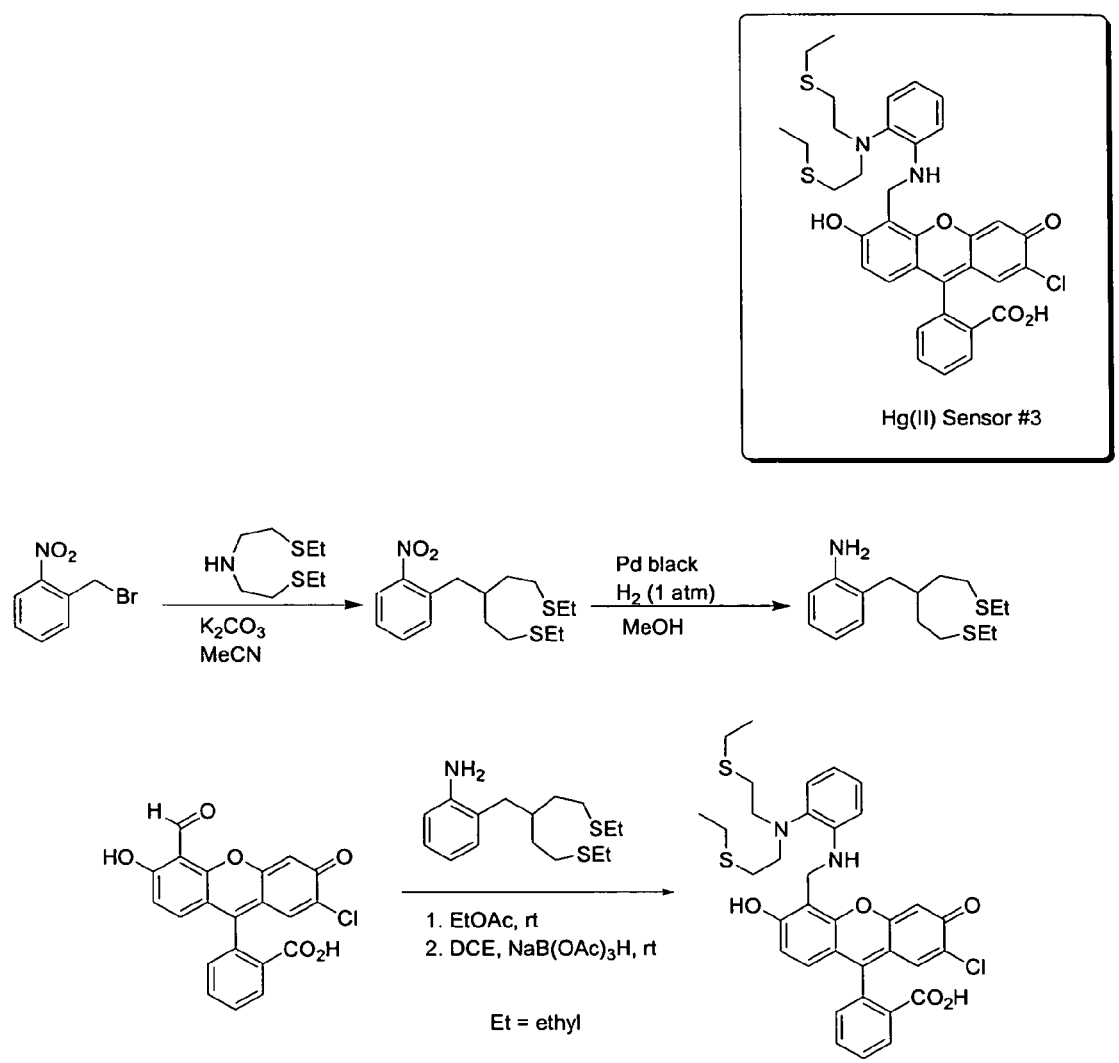
Figure 14:
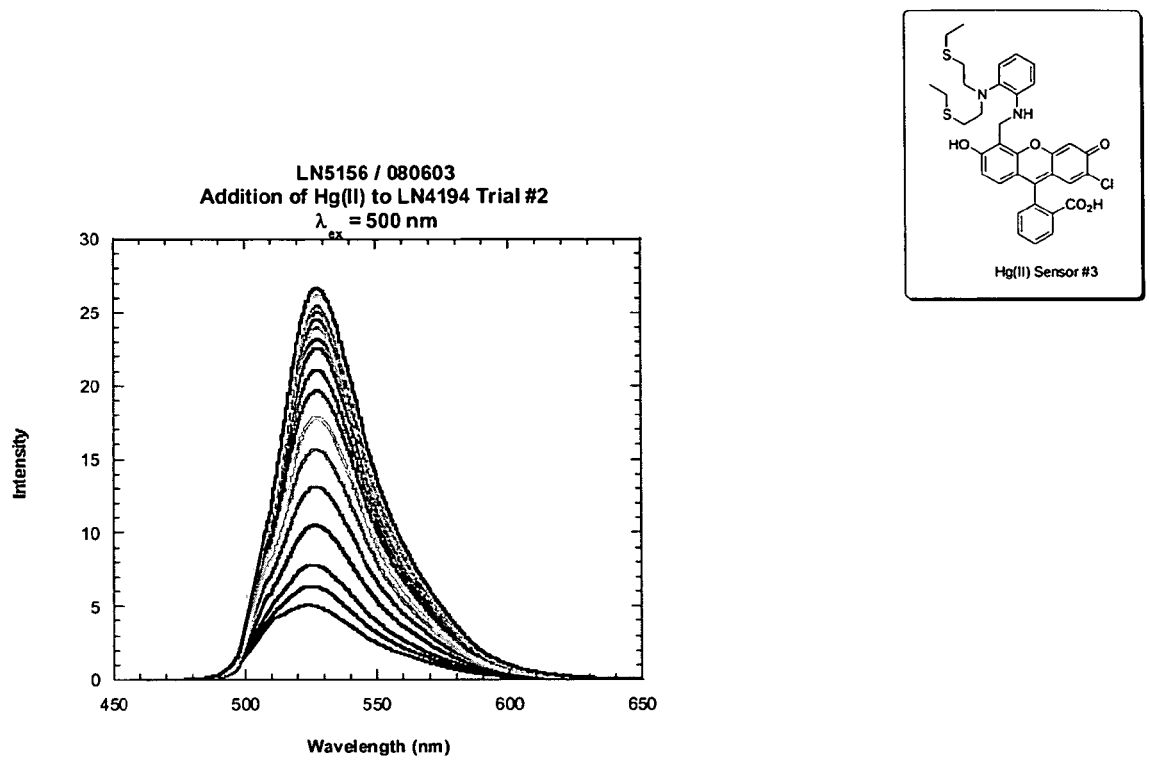
Figure 15:
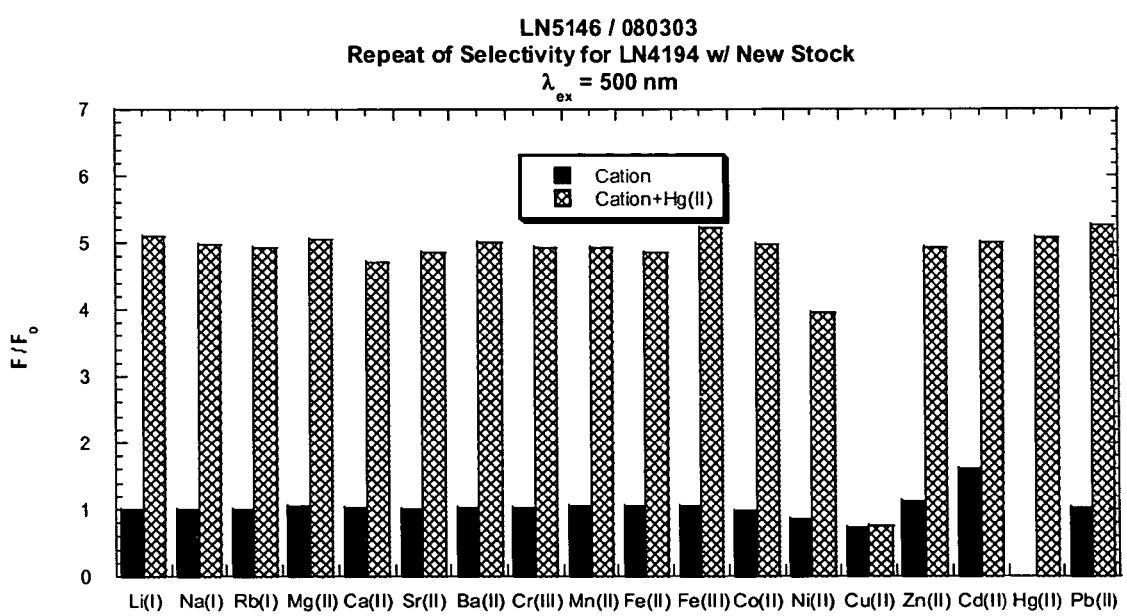
Figure 16:
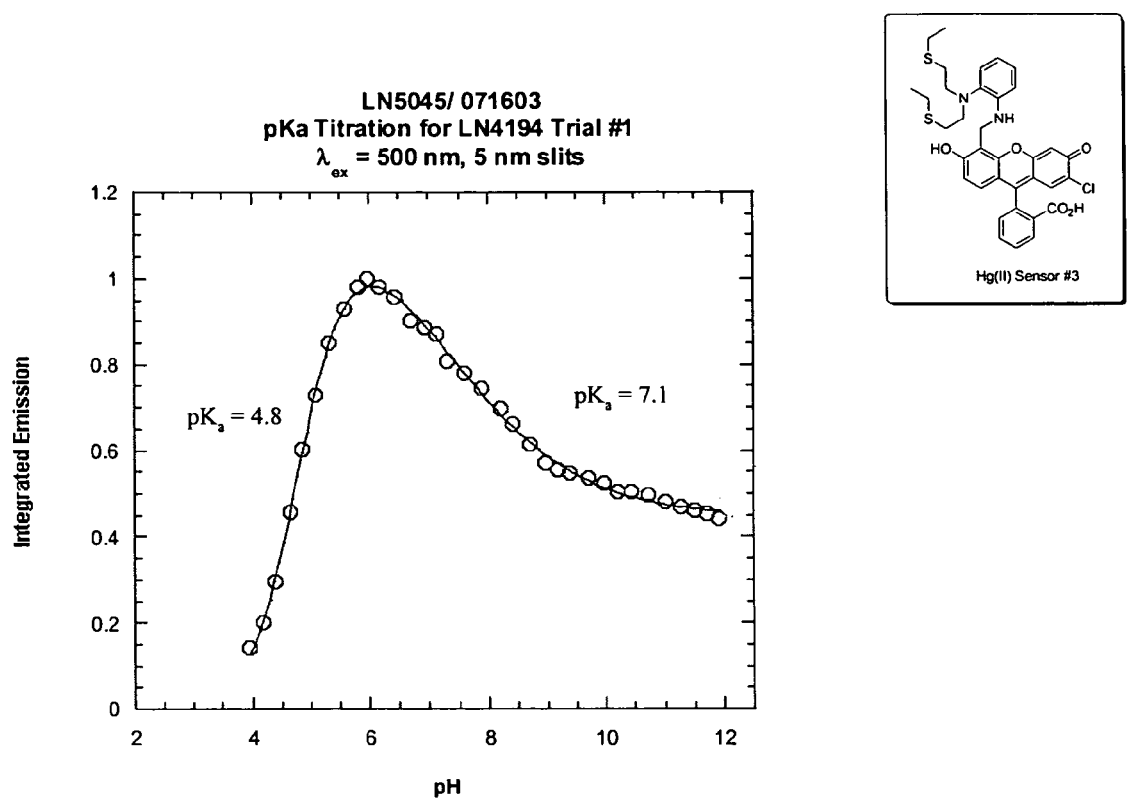
Figure 17:
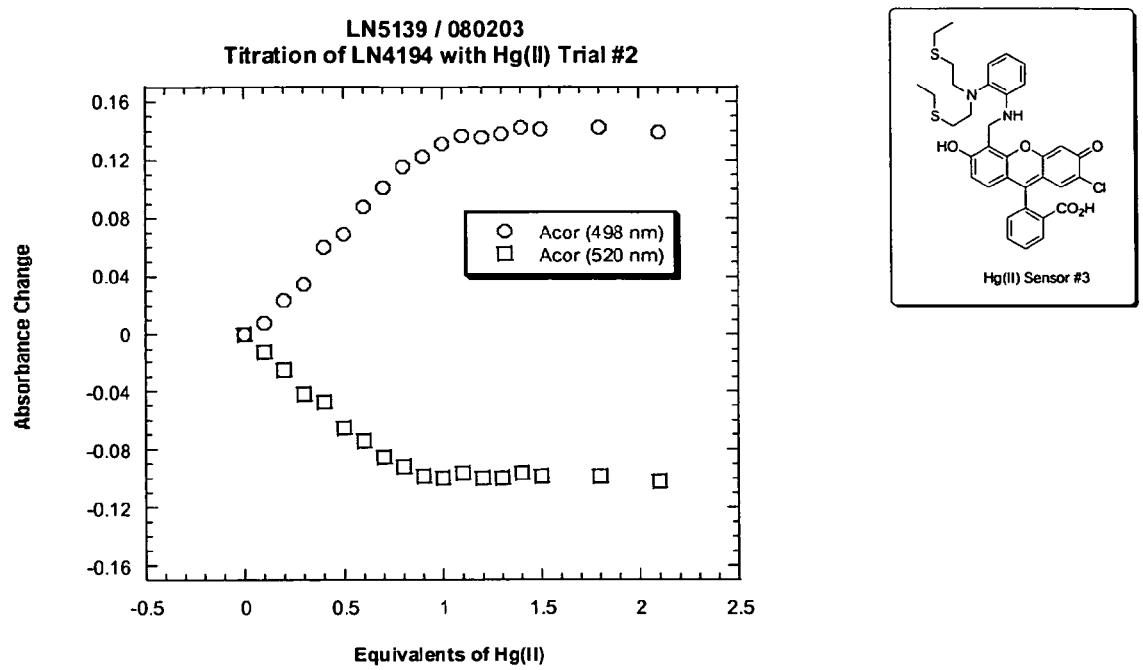
Figure 18:
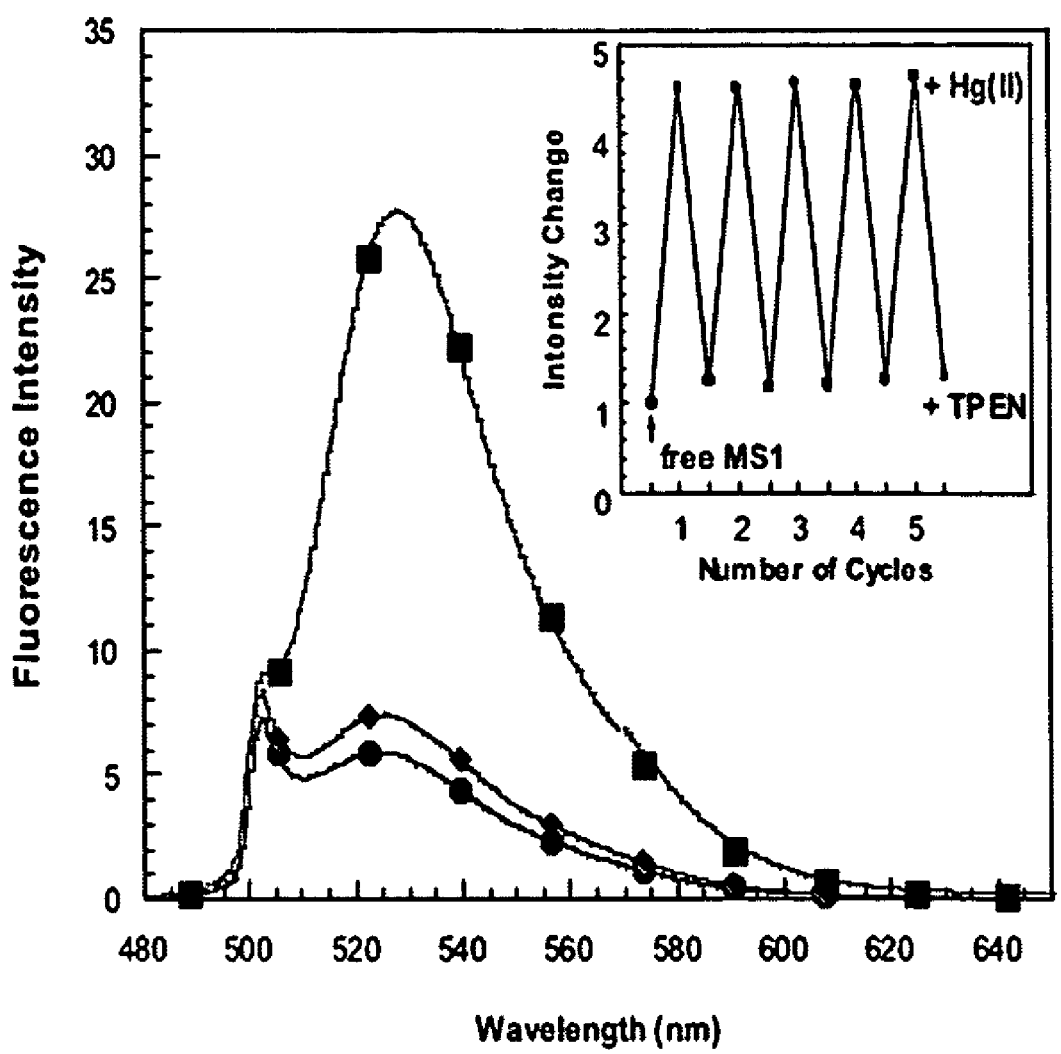
Figure 19:
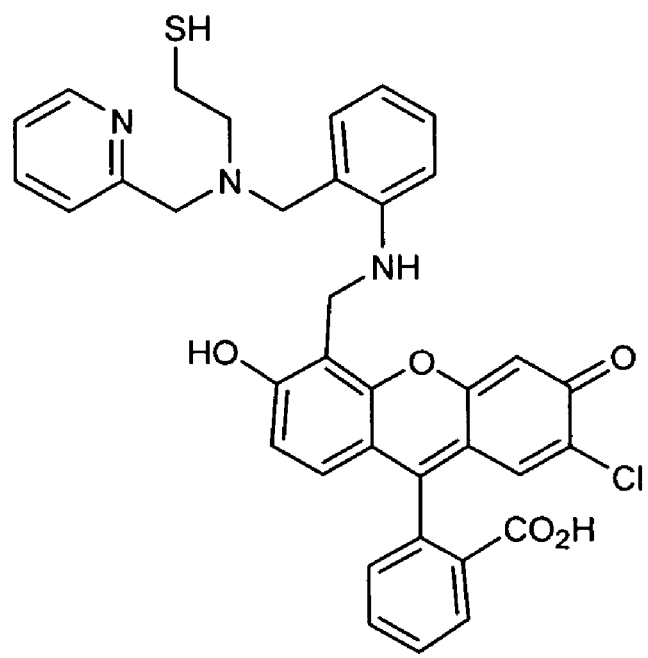

Examples 3 through 5 are depicted in the schematic of FIG. 13.

EXAMPLE 3

N-(2-Nitrobenzyl)-3,9-dithia-6-azaundecane (1). 2-Nitrobenzylbromide (560 mg, 2.59 mmol), $K_2CO_3$ (400 mg, 2.89 mmol) and molecular sieves were combined in 25 mL of $CH_3CN$ and stirred. A 10 mL solution of 3,9-dithia-6-azaundecane (501 mg, 2.59 mmol) in $CH_3CN$ was added dropwise. The reaction was stirred for 8 h, filtered through Celite and the solvent was evaporated to afford a yellow oil. The oil was flushed through a short silica plug (7:1 hexanes:EtOAc) and dried to yield the product (726 mg, 85%). TLC $R_f$=0.38 (silica, 7:1 hexanes:EtOAc). $^1H$ NMR ($CDCl_3$, 300 MHz) δ $^{13}C$ NMR ($CDCl_3$, 125 MHz) δ 14.86, 26.03, 29.06, 54.03, 55.55, 124.10, 127.65, 130.68, 132.35, 134.68, 149.23. HRMS (ESI) Calcd for $MH^+$, 329.1352; Found, 329.1359.

EXAMPLE 4

N-(2-Aminobenzyl)-3,9-dithia-6-azaundecane (2). A portion (512 mg) of Pd black was placed in a flask purged with Ar after which 10 mL of MeOH was added. N-(2-Nitro-benzyl)-3,9-dithia-6-azaundecane (1, 301 mg, 920 μmol) dissolved in MeOH (20 mL) was transferred to the reaction flask with a syringe. Hydrogen was introduced to the reaction with vigorous stirring for 7 h. After purging with Ar, the solution was filtered through Celite and the solvent was removed in vacuo to yield a brown oil. The crude material was purified by flash chromatography on silica (7:1 hexanes:EtOAc), which afforded a yellow oil (84 mg, 31%). TLC $R_f$=0.33 (silica, 7:1 hexanes:EtOAc). $^1H$ NMR ($CDCl_3$, 300 MHz) δ 1.21 (6H, t), 2.47 (4H, q), 2.71 (8H, m), 3.64 (2H, s), 4.75 (2H of $NH_2$, s), 6.64 (2H, m), 6.97 (1H, d), 7.08 (1H, td). $^{13}C$ NMR ($CDCl_3$, 125 MHz) δ 14.63. 25.71, 28.86, 52.93, 58.00, 115.12, 117.09, 121.93, 128.09, 129.98, 146.59. HRMS (ESI) Calcd for $MNa^+$, 321.1430; Found, 321.1427.

EXAMPLE 5

2-{5-[(2-{[Bis-(2-ethylsulfanyl-ethyl)-amino]-methyl}-phenylamino)-methyl]-2-chloro-6-hydroxy-3-oxo-3H-xanthen-9-yl}-benzoic acid (MS1). A portion (73 mg, 245 μmol) of N-(2-aminobenzyl)-3,9-dithia-6-azaundecane, 2, was dissolved in 3 mL of EtOAc and 7'-chloro-4'-fluoresceincarboxaldehyde (97 mg, 245 μmol) was added. The reaction became orange-pink and cloudy. An additional 1 mL of EtOAc was added and the mixture was stirred at room temperature for 18 h. During this time, the solution clarified and turned red. The EtOAc was removed to yield a magenta foam, which was dried in vacuo. The dried foam was dissolved in 3 mL of 1,2-dichloroethane, $NaB(OAc)_3H$ (65 mg, 307 μmol) was added, and the reaction was left to stir overnight at room temperature. The solution was diluted with 5 mL of $CH_2Cl_2$, extracted (3×8 mL) with saturated $NaHCO_3$, and washed (2×8 mL) with deionized water. The organic layer was dried over $MgSO_4$ and the solvent was removed under reduced pressure to yield the crude product as a red solid. Chromatography on silica gel (50:1 $CHCl_3$:MeOH) followed by preparative TLC using the same solvent system yielded the purified product as a deep magenta solid (88 mg, 52%). TLC $R_f$=0.41 (silica, 9:1 $CHCl_3$:MeOH); mp=58-61° C. $^1H$ NMR ($CD_3OD$, 300 MHz) δ 1.02 (6H, t), 2.24 (4H, q), 2.2.38 (4H, m), 2.57 (4H, m), 3.59 (2H, s), 4.46 (1H, d), 4.4.60 (1H, d), 6.58 (2H, m), 6.68 (1H, s), 6.95-7.11 (4H, m), 7.20 (1H, m), 7.29 (1H, d), 7.57 (2H, m), 8.03 (1H, d). $^{13}C$ NMR (DMF-$d_7$, 125 MHz) δ 14.81, 25.53, 28.28, 40.63, 53.95, 58.03, 103.64, 108.83, 110.31, 110.81, 112.69, 115.17, 122.69, 122.87, 126.48, 128.07, 128.21, 128.61, 128.69, 129.68, 129.89, 130.08, 130.75, 135.18, 170.66, 173.15. FTIR (KBr, $cm^{-1}$) 3423, 3049, 2963, 2919, 1647, 1607, 1571, 1509, 1458, 1374, 1342, 1302, 1220, 1149, 1044, 1007, 937, 883, 828, 746, 714, 689, 621, 598, 547, 469. HRMS (ESI) Calcd for MNa+, 699.1725; Found, 699.1720.

EXAMPLE 6

General Spectroscopic Procedures. Ultrol grade PIPES (piperazine-N,N'-bis(2-ethanesulfonic acid) from Calbiochem, KCl (99.997%) and anhydrous $HgCl_2$ (99.998%) were purchased and used as received. Millipore filtered water was used to prepare all aqueous solutions. With the exception of the $pK_a$ determination, all spectroscopic measurements were conducted at neutral pH with 50 mM PIPES, 100 mM KCl buffer adjusted to pH 7. An Orion glass electrode, calibrated prior to use, was employed to record solution pH. Mercury solutions were prepared from 10 mM stock solutions of $HgCl_2$. Stock solutions of MS1 (1 mM in DMSO) was prepared, stored at −4° C., and thawed in the dark immediately prior to use. After addition of this stock solution to aqueous buffers, the resulting solution contained 0.1% DMSO for fluorescence and 1% DMSO for absorption measurements. The KaleidaGraph software package was used to manipulate all spectral data.

EXAMPLE 7

Optical Absorption Spectroscopy. UV-visible spectra were obtained by using either a Cary IE scanning spectrophotometer or a Hewlet Packard diode array spectrophotometer. Both instruments were controlled by Pentium PCs and were run using the manufacturer supplied software packages. A circulating water bath was used during acquisition to maintain the temperature at 25.0° C.±1.0° C. Samples were contained in 1-cm path length quartz cuvettes (3.5 mL volume). All manipulations were performed at least three times.

EXAMPLE 8

$Hg^{2+}$ Binding Studies by Absorption Spectroscopy. Metal binding titrations and Job plots were obtained for MS1 in order to determine the stoichiometry of the metal-bound complex in solution. In a typical titration, 3 μL aliquots of a 1 mM $HgCl_2$ solution in water were added to a solution of 10 μM MS1 and the absorbance changes at 498 and 520 nm were plotted against equivalents of $Hg^{2+}$ added.

EXAMPLE 9

Fluorescence Spectroscopy. Emission spectra were obtained with a Hitachi F-3010 spectrofluorimeter linked to a Pentium PC running the SpectraCalc software package. A rhodamine quantum counter was used to normalize the spectra for excitation intensity, and manufacturer-supplied correction curves were used to normalize the emission spectra. Manufacturer supplied photomultiplier curves were used to correct for emission intensity. A circulating water bath was used during all experiments to regulate the temperature at 25.0° C.±0.1° C. Spectra were obtained with 3 nm slit widths and either a 240 nm/min or 600 nm/min scan speed. All measurements were conducted at least in triplicate.

EXAMPLE 10

Quantum Yield Measurements. The quantum yield of MS1 was determined by comparison to fluorescein in 0.1 N NaOH ($\phi$=0.95) as a reference. In a typical experiment, a 6 mL solution of ~1 μM MS1 was prepared. For metal-free studies, 10 μL of 100 mM $K_4$EDTA was added to chelate any adventitious metal ions. To determine the quantum efficiencies of the metal-bound dye, 10 μL of a 10 mM $HgCl_2$ solution was added to a 1 μM MS1 solution. The concentration of the reference solution was adjusted such that $A_{max}$ (490 nm) equaled $A_{max}$ of MS1 (505 nm) or $A_{max}$ of the $Hg^{2+}$ complex (501 nm), and the excitation wavelength was chosen as the wavelength determined from where the reference and probe excitation spectra intersect. Excitation was at 497 nm for MS1 and at 496 nm for the $Hg^{2+}$ complex. Emission spectra were integrated from 510-650 nm and the quantum yields were calculated standard methods.

Figure 2:
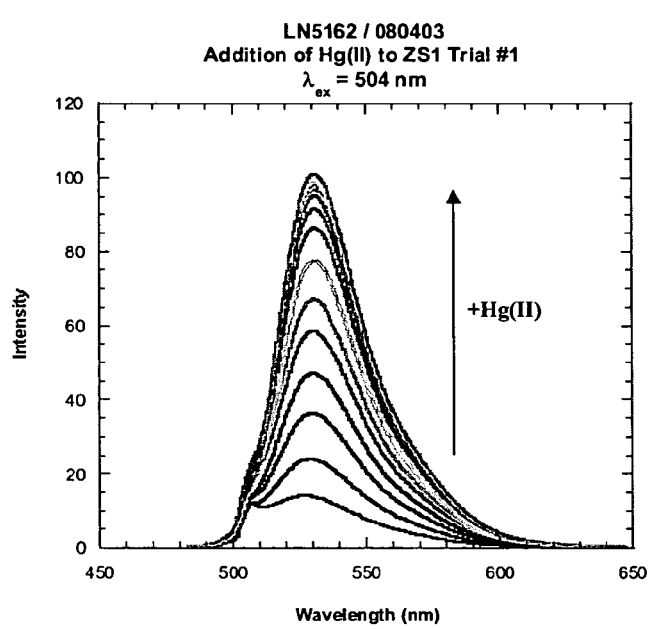
Figure 2:
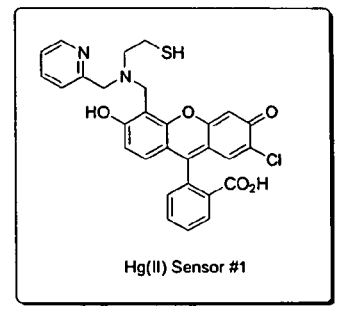

At pH 7 and 100 mM ionic strength (50 mM PIPES buffer, 100 mM KCl), and in the presence of EDTA to scavenge any adventitious metal ions, MS1 exhibits an emission maximum at 524 nm and a quantum yield of 0.04. The low quantum yield of the unbound sensor results from PET (photoinduced electron transfer) quenching of the fluorescein emission by the lone pair of the aniline nitrogen atom. This nitrogen atom has a $pK_a$ of 7.1, which indicates that the deprotonation equilibrium allows efficient PET quenching at neutral pH. Upon disruption of this quenching pathway by $Hg^{2+}$ coordination, the emission maximum red-shifts slightly to 528 nm and the quantum yield increases ~2.75-fold to 0.11. The absorption spectrum exhibits a blue-shift from 505 nm ($\epsilon$=61,300 $M^{-1}$ $cm^{-1}$) to 501 nm ($\epsilon$=73,200 $M^{-1}$ $cm^{-1}$) upon $Hg^{2+}$ binding, resulting in a ~3.3-fold increase in brightness. A ~5-fold increase in integrated emission is observed upon addition of $Hg^{2+}$ (FIG. 2). Metal binding titrations indicate that MS1 forms a 1:1 complex with $Hg^{2+}$ in solution, which is responsible for the fluorescence enhancement, with an $EC_{50}$ of 410 nM.

EXAMPLE 11

Determination of Protonation Constants. The $pK_a$ values for MS1 affect fluorescence were determined by plotting the integrated emission intensity versus pH from ~12 to ~4. In a typical experiment, a 30 mL solution of 1 μM MS1 in 100 mM KCl, 10 mM KOH was prepared (pH ~12). Aliquots of 6 N, 2 N, 1 N, 0.5 N, and 0.5 N HCl were added to achieve pH changes of approximately 2.5, and the emission spectrum was recorded after each addition. The overall volume change for each experiment did not exceed ~2%. Upon excitation at 500 nm, the emission spectra were integrated over the range 510 nm to 650 nm, normalized and plotted against pH. The data were fit to the non-linear expression previously described.

EXAMPLE 12

Selectivity of Mercury-Induced Fluorescence in the Presence of Other Metal Ions. The selectivity of MS1 for $Hg^{2+}$ against a background of various alkali, alkaline earth, transition metal ions, and Zn(II), Cd(II) or Pb(II) was investigated by using fluorescence spectroscopy. Aqueous metal ion solutions of Li(I), Na(I), Rb(I), Mg(II), Ca(II), Sr(II), Ba(II), Mn(II), Co(II), Ni(II), Cd(II), and $Hg^{2+}$ were prepared from the chloride salts. The Cu(II) solution was prepared from copper sulfate and the Pb(II) was prepared from lead nitrate. A solution of Cr(III) was prepared from chromium acetate and stored at pH 1. Solutions of Fe(II) were prepared immediately before use with ferrous ammonium sulfate and water that was thoroughly purged with Ar. All stock solutions were ~10 mM, with the exception of 100 mM NaCl. In a typical experiment, the emission spectrum of the free dye was recorded. A 20 μL aliquot of a ~10 mM metal solution was then added to a 1 μM solution of MS1 (3 mL, for a concentration of metal ion at about 1 to about 50 ppm, depending on the molecular weight of the metal ion tested) and the emission spectrum was recorded with excitation at 500 nm. Subsequently, a 20 μL portion of 10 mM $HgCl_2$ was added and the emission spectrum was obtained. The spectra were integrated from 510-650 nm and normalized with respect to the free dye.

Figure 3:
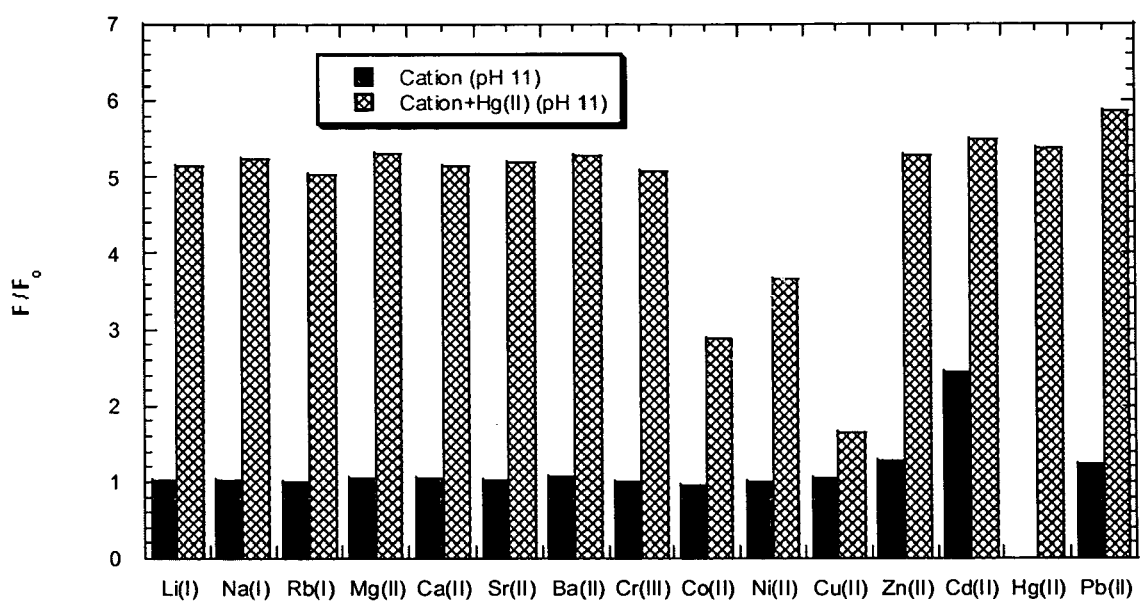
Figure 4:
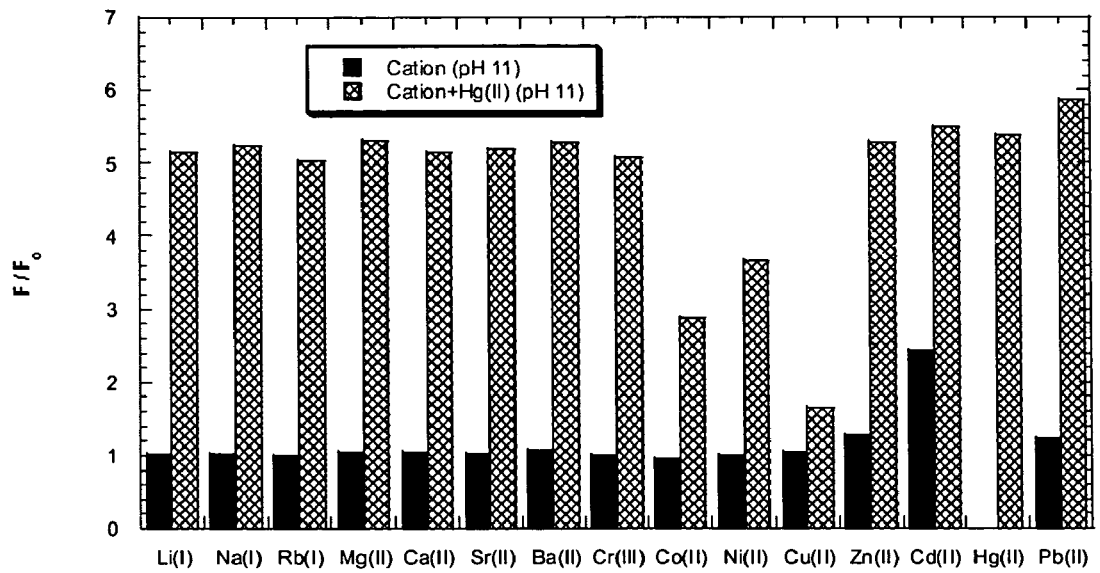
Figure 5:
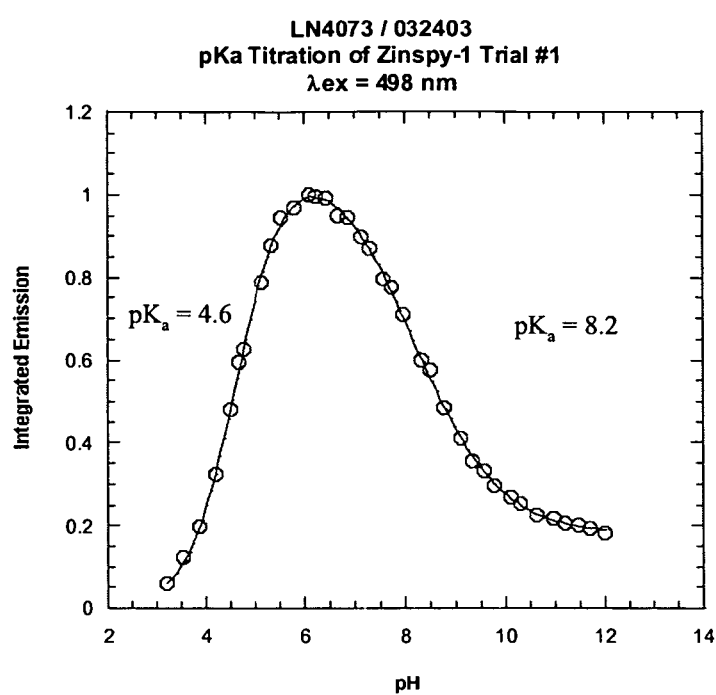
Figure 5:
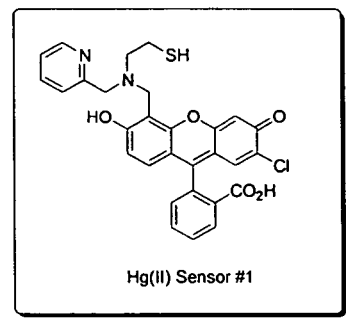
Figure 6:
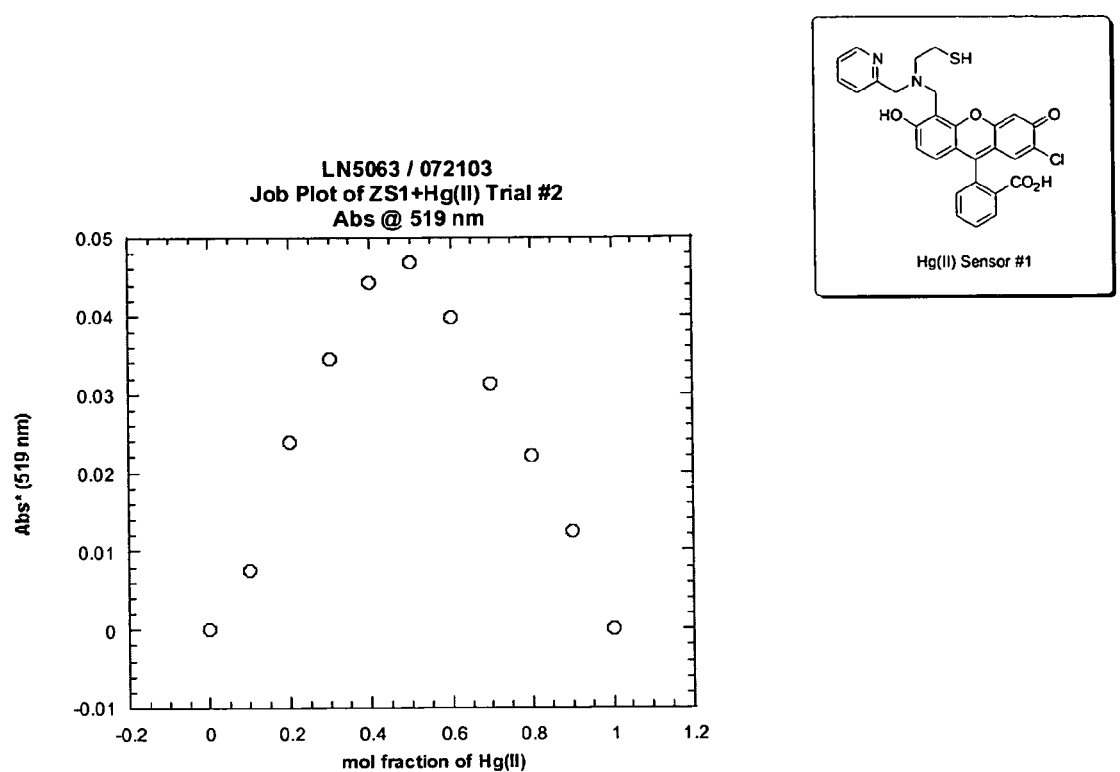
Figure 7:
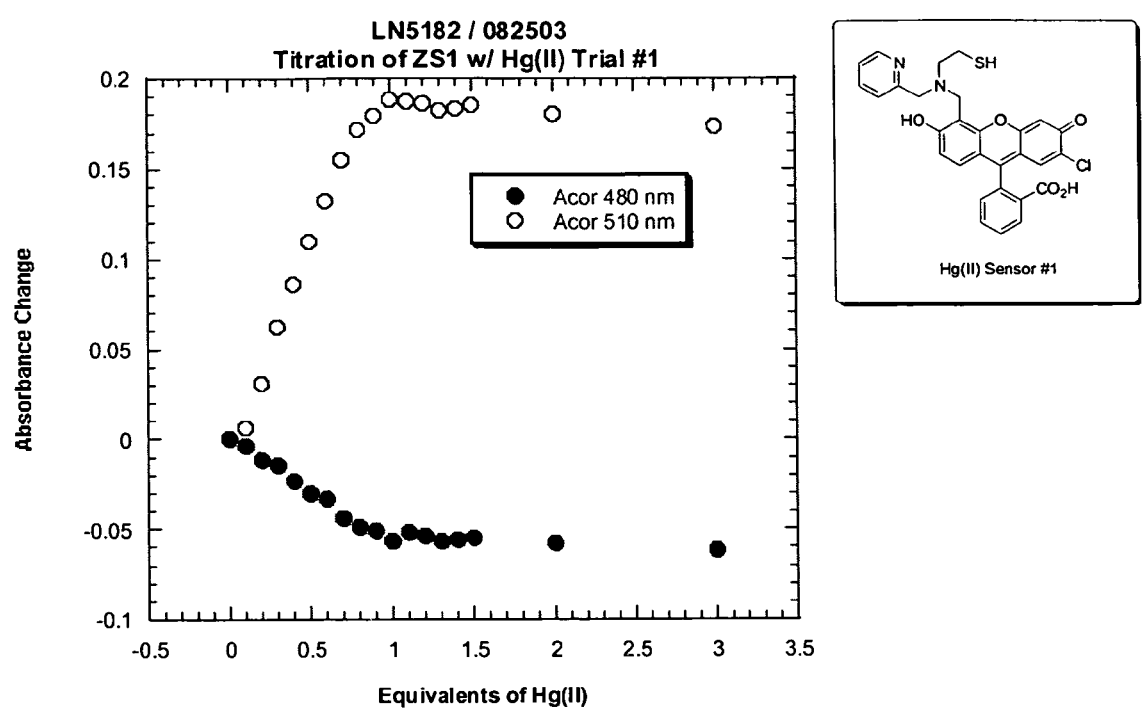
Figure 8:
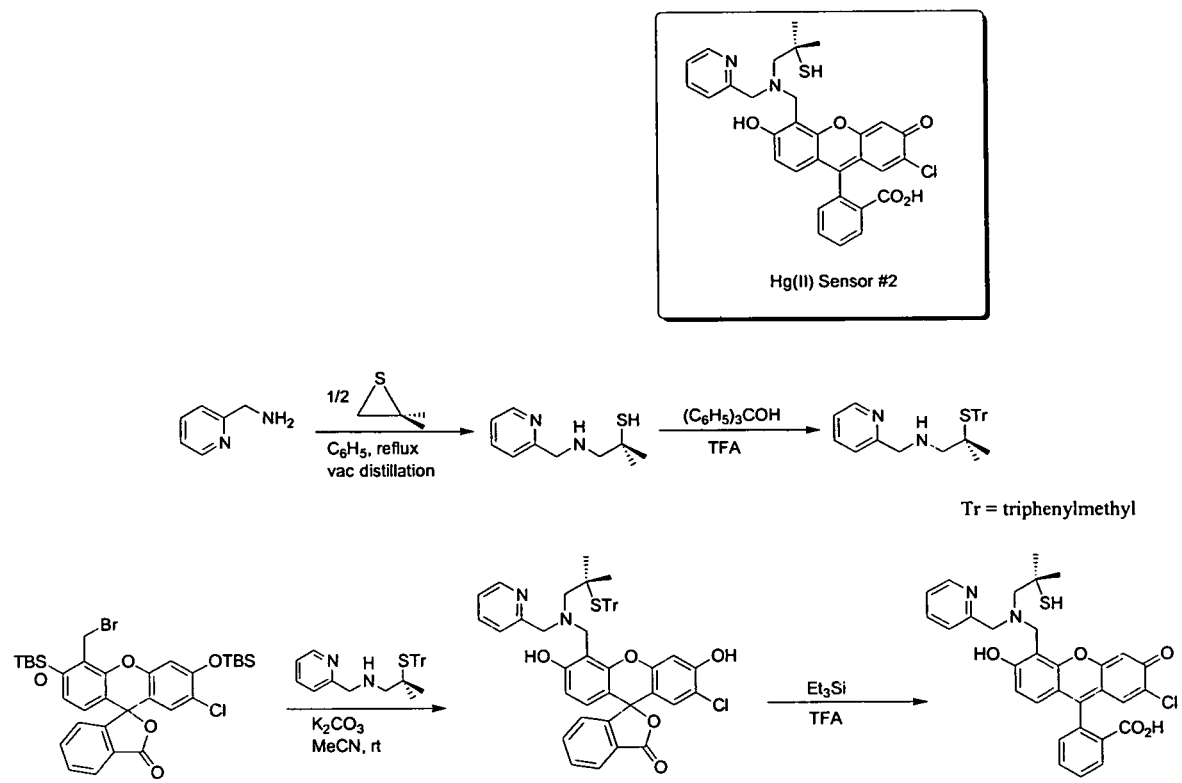
Figure 9:
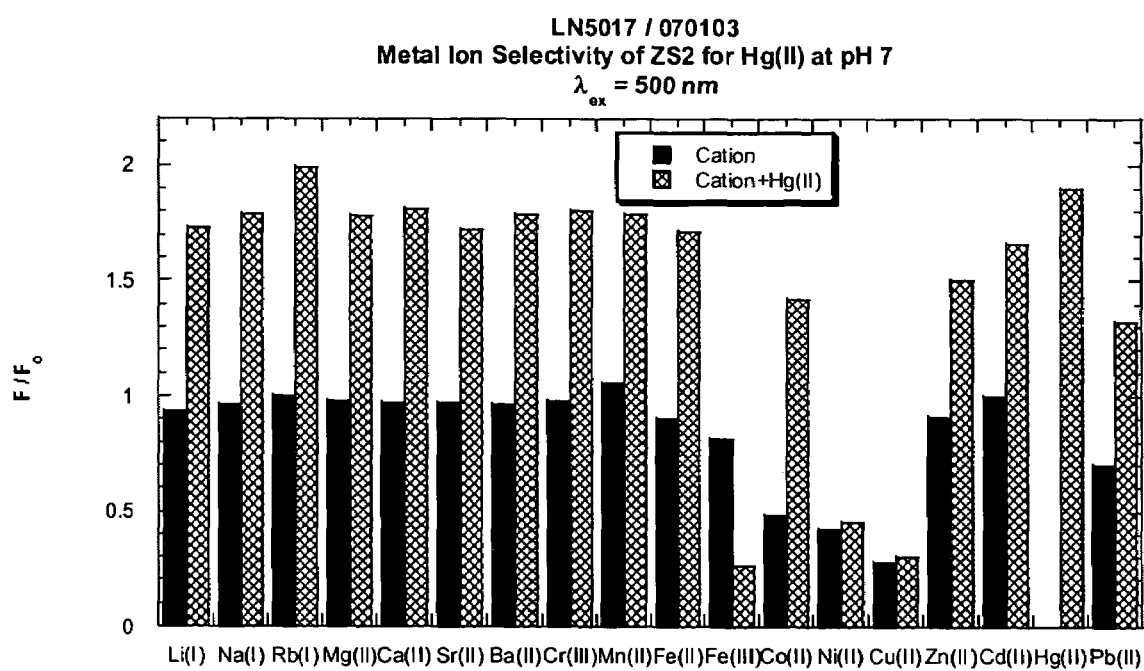
Figure 10:
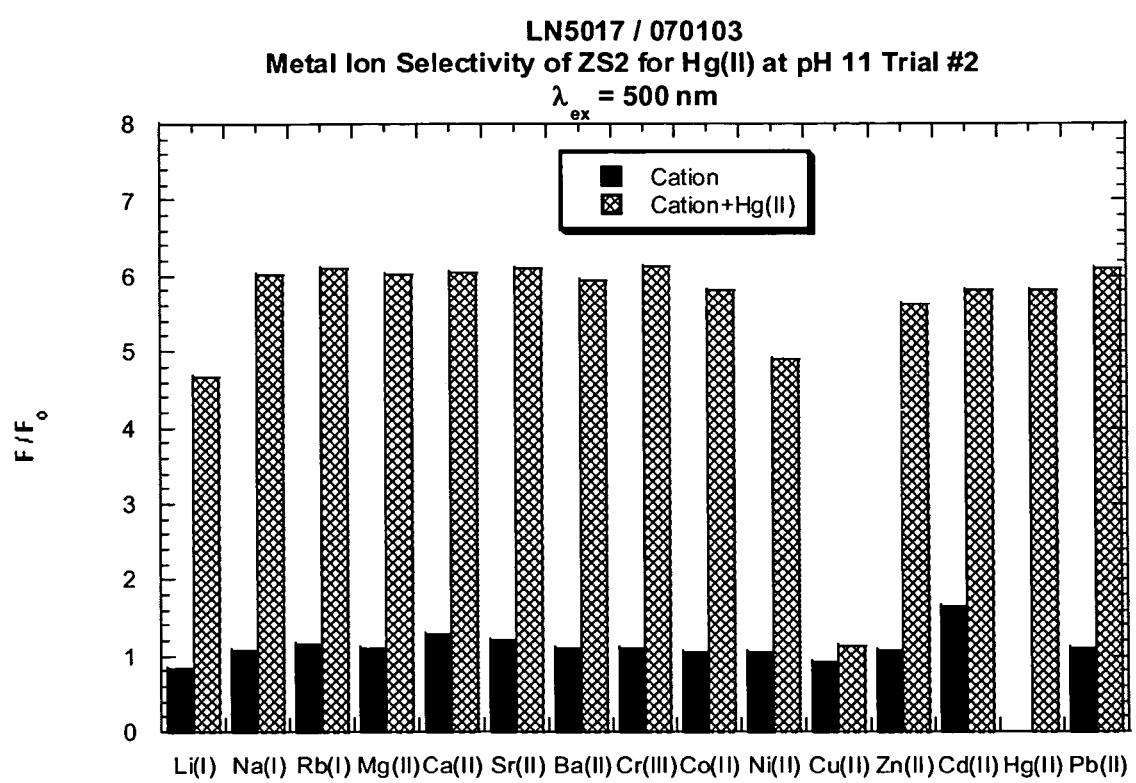
Figure 11:
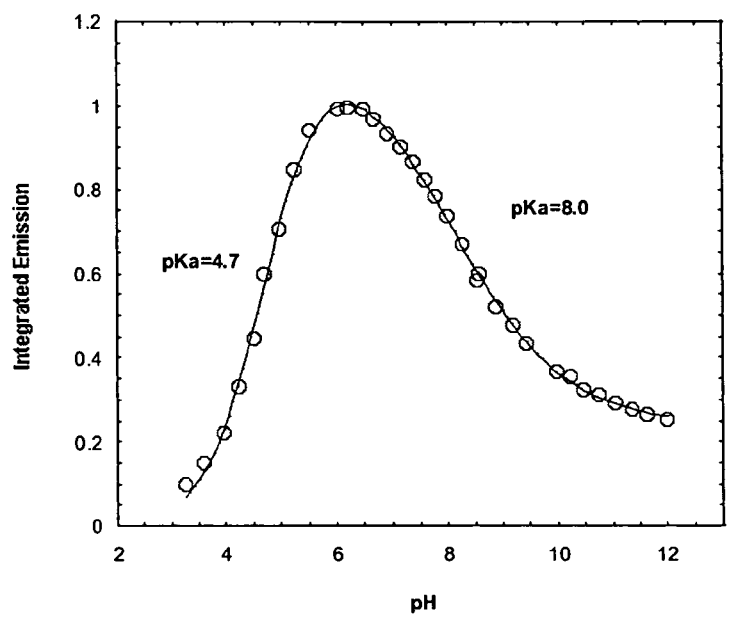
Figure 11:
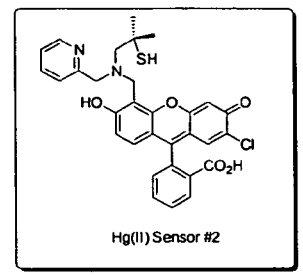
Figure 12:
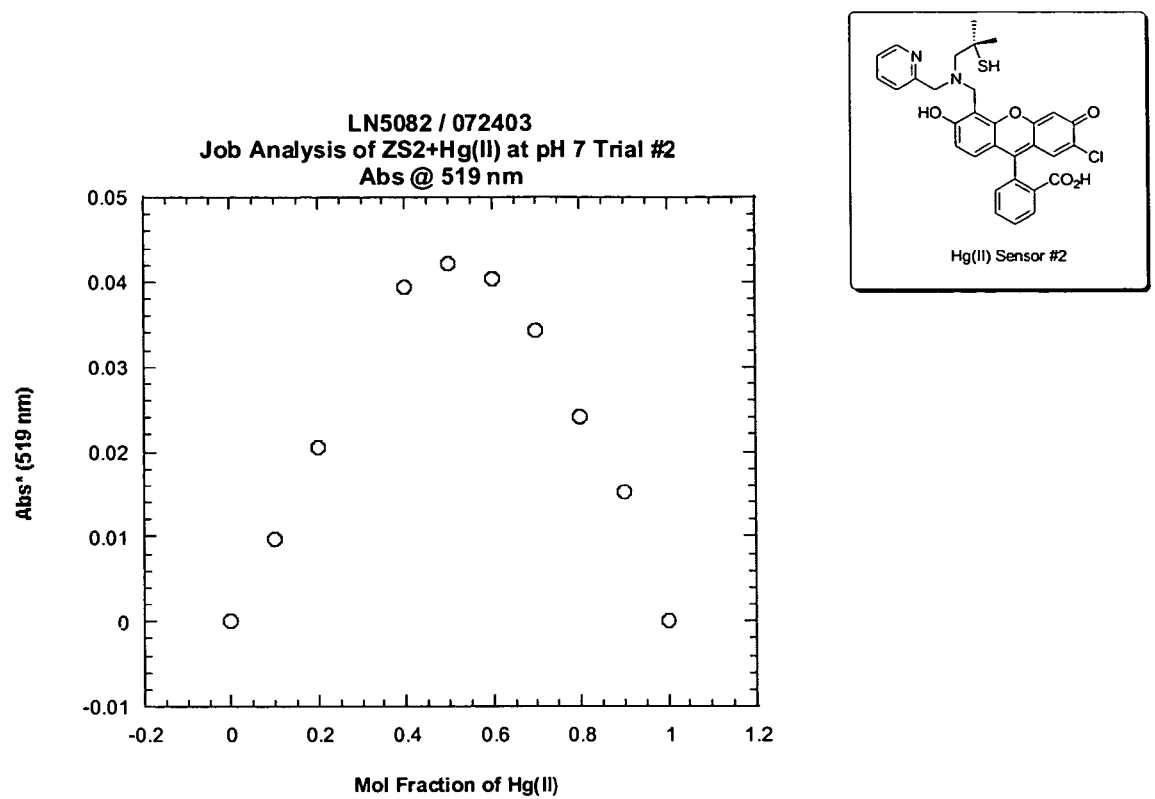

The fluorescence response of MS1 to various cations and its selectivity for $Hg^{2+}$ are illustrated in FIGS. 3 and 4. The Hg response of MS1 is unaffected in a background of environmentally relevant alkali and alkaline earth metals including Li(I), Na(I), Rb(I), Mg(II), Ca(II), Sr(II) and Ba(II). The Group 12 metals Zn(II) and Cd(II), in addition to Cr(III) and Pb(II), do not inhibit the fluorescence response of MS1 to $Hg^{2+}$. Of the first-row transition metal ions considered, only Cu(II) interferes with the $Hg^{2+}$-induced fluorescence increase. MS1 binds $Hg^{2+}$ reversibly. Addition of 1 equivalent of the heavy metal ion chelator N',N',N'',N''-tetra(2-picolyl)ethylenediamine (TPEN) to a stoichiometric mixture of MS1 and $Hg^{2+}$ results in an immediate fluorescence decrease to within ~20% of the background value. This on/off behavior can be reversed by introduction of another equivalent of $Hg^{2+}$, restoring the fluorescence attributed to $Hg^{2+}$ complexation.

The EPA standard for the maximum allowable level of inorganic $Hg^{2+}$ in drinking water is 2 ppb. When MS1 is added to an aqueous solution containing 2 ppb of $Hg^{2+}$, a fluorescence increase of 11.3±3.1% is observed, indicating that MS1 can detect environmentally relevant concentrations of $Hg^{2+}$. (Average of 28 independent trials with a range of 9.1 to 15.9%; [MS1]=500 nM). A highly sensitive and selective fluorescein-based probe for $Hg^{2+}$ that is water-soluble and gives a positive response upon analyte binding, such as MS1, may be of some practical utility.

7. REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Frederickson et al. *J. Neurosci. Meth.* 1987, 20, 91-103; Zalewski et al. *Biochem. J.* 1993, 296, 403-408; Mahadevan et al. *Aust. J. Chem.* 1996, 49, 561-568; Budde et al. *Neuroscience* 1997, 79, 347-358; Canzoniero et al. *Neurobiology of Disease* 1997, 4, 275-279; Fahrni et al. *J. Am. Chem. Soc.* 1999, 121, 11448-11458; Nasir et al. *JBIC* 1999, 4, 775-783; Belgodere et al. *Heterocycles* 1985, 23, 349-354; Romary et al. *J. Chem. Soc (C)* 1968, 2884-2887; da Mota et al. *J. Chem. Soc. (A)* 1969, 2036-2042; Hörlein, U. *Chemische Berichte* 1954, 87, 463-472; Houser et al. *J. Am. Chem. Soc.* 1995, 117, 10745-10746; Kovacs, Z.; Sherry, A. D. *Tet. Lett.* 1995, 51, 9269-9272; Prasad et al. *J. Chem. Soc. Perkin Trans.* 1991, 3329-3332; Vallee et al. *Physiol. Rev.* 1993, 73: 79-118; Lippard et al. *Principles of Bioinorganic Chemistry*; 1st ed.; University Science Books: Mill Valley, 1994; Frederickson, C. *Int. Rev. Neurobiol.* 1989, 31: 145-238 Huang, E. *Proc. Natl. Acad. Sci. U.S.A.* 1997, 94: 13386-13387; Nasir, et al. *JBIC* 1999, 4: 775-783; Frederickson et al. *Biol. Signals* 1994, 3: 127-139; Budde et al. *Neuroscience* 1997, 79: 347-358; Harrison et al. *Neuropharmacology* 1994, 33: 935-952; Choi et al. *Ann. Rev. Neurosci.* 1998, 21: 347-375; Cuajungco et al. *Neurobiology of Disease* 1997, 4: 137-169; Palmiter et al. *EMBO J.* 1995, 14: 639-649; Palmiter, et al. *EMBO J.* 1996, 15: 1784-1791; Palmiter, et al. *Proc. Natl. Acad. Sci. USA* 1996, 93: 14934-14939; Ebadi, et al. *Methods Enzymol.* 1991, 205: 363-387; Ebadi, et al. *Neurochem. Int.* 1995, 27: 1-22; Ebadi, et al. *J. Neurochem.* 1996, 66: 2121-2127; Evans, I. *J. Org. Chem.* 1959, 24: 863; Palmiter, et al. *Proc. Natl. Acad. Sci. USA* 1992, 89: 6333-6337; Pountney, et al. *FEBS Lett.* 1994, 345: 193-197; Tsuji, et al. *EMBO J.* 1992, 11: 4843-4850; Uchida, et al. *Neuron* 1991, 7: 337-347; Slomianka, L. *Neuroscience* 1992: 48, 325-352; Atar, et al. *J. Biol. Chem.* 1995, 270: 2473-2477; de Silva et al. *Chem. Rev.* 1997, 97: 1515-1566; Tsien, R. Y. *Fluorescent and Photochemical Probes of Dynamic Biochemical Signals Inside Living Cells;* Czarnik, A. W., Ed.; American Chemical Society: Washington D.C., 1993; Vol. 538, pp 130-146.; Czarnik, A. W. *Curr. Biol.* 1995, 2: 423-428; Frederickson, et al. *J. Neurosci. Meth.* 1987, 20: 91-103; Walkup et al. *J. Am. Chem Soc.* 2000, 122: 5644-5645; Lakowicz, J. R. *Principles of Fluorescence Spectroscopy;* 2nd ed.; Kluwe Academic/Plenum: New York, 1999; Gruenwedel, D. W. *Inorg. Chem.* 1968, 7: 495-501; SMART; 5.05 ed.; Bruker AXS, Inc.: Madison, Wis., 1998; Feig et al. *Inorg. Chem.* 1996, 25: 6892-6898; McBryde, W. A. E. *Talanta* 1974, 21: 979-1004; Walkup et al. *J. Am. Chem Soc.* 2000: 122: S1-S7; Burton et al. *J. Soc. Chem. Ind. London* 1948: 67: 345; Wolf, H. U. *Experientia* 1973, 29: 241-249; Anderegg et al. *Helv. Chim. Acta* 1977, 60: 123-140; Sen, et al. *J. Indian Chem. Soc.* 1929, 6, 505; Sen, et al. *J. Indian Chem. Soc.* 1929, 6, 51; Job, A., *Ann. Chem. (Paris)* 1928, 9, 113-203; Burdette, S. C., et al. *J. Am. Chem. Soc.* 2001, in press; U.S. Pat. No. 6,013,802; U.S. Pat. No. 6,083,758; U.S. Pat. No. 6,063,637; U.S. Pat. No. 5,986,094; U.S. Pat. No. 5,756,771; U.S. Pat. No. 4,510,251; Renzoni, A. Zino, F.; Franchi, E. *Environ. Res.* 1998, 77, 68-72; Malm, O. *Environ. Res.* 1998, 77, 73-78; "EPA Fact Sheet (EPA-823-F-01-011). Mercury Update: Impact on Fish Advisories," EPA, Office of Water, 2001; Boening, D. W. *Chemosphere* 2000, 40, 1335-1351; Nendza, M.; Herbst, T.; Kussatz, C.; Gies, A. *Chemosphere* 1997, 35, 1875-1885; Hardy, S.; Jones, P. *J. of Chromatography A* 1997, 791, 333-338; Eyssen, G. E. M.; Ruedy, J.; Neims, A. *Am. J. Epidemol.* 1983, 118, 470-479; Davidson, P. W. Myers, G.; Cox, C. Shamlaye, C. F.; Marsh, D. O.; Tanner, M. A.; Berlin, M.; Sloane-Reeves, J.; Cemichiari, E.; Choisy, O.; Choi, A.; Clarkson, T. W. *Neurotoxicol.* 1995, 16, 677-688; Grandjean, P. Weihe, P.; White, R. F.; Debes, F. *Environ. Res.* 1998, 77, 165-172; Takeuchi, T. Morikawa, N.; Matsumoto, H.; Shiraishi, Y. *Acta Neuropathol.* 1962, 2, 40-57; Matsumoto, H. Koya, G.; Takeuchi, T. et. al. *J. Neuropathol. Exp. Neurol.* 1965, 24, 563-574; Harada, M. *Crit. Rev. Toxicol.* 1995, 25, 1-24; Choi, M. J. Kim, M.-Y.; Chang, S.-K. *Chem. Commun.* 2001, 1664-1665; Brümmer, O.; La Clair, J. J.; Janda, K. D. *Org. Lett.* 1999, 1, 415-418; Sancenón, F.; Martinez-Máñez, R.; Soto, J. *Chem. Commun.* 2001, 2262-2263; Sancenón, F.; Martinez-Máñez, R.; Soto, J. *Tetrahedron Lett.* 2001, 42, 4321-4323; Prodi, L.; Bargossi, C.; Montalti, M.; Zaccheroni, N.; Su, N.; Bradshaw, J. S.; Izatt, R. M.; Savage, P. B. *J. Am. Chem. Soc.* 2000, 122, 6769-6770; Rurack, K.; Resch-Genger, U.; Bricks, J. L.; Spieles, M. *Chem. Commun.* 2000, 2103-2104; Hennrich, G.; Sonnenschein, H.; Resch-Genger, U. *J. Am. Chem. Soc.* 1999, 121, 5073-5074; Rurack, K.; Kollmannsberger, M.; Resch-Genger, U.; Daub, J. *J. Am. Chem. Soc.* 2000, 122, 968-969; Chae, M.-Y.; Czarnik, A. W. *J. Am. Chem. Soc.* 1992, 114, 9704-9705; Yoon, J.; Ohler, N. E.; Vance, D. H.; Aumiller, W. D.; Czarnik, A. W. *Tetrahedron Lett.* 1997, 28, 3845-3848; Winkler, J. D.; Bowen, C. M.; Michelet, V. *J. Am. Chem. Soc.* 1998, 120, 3237-3242; Unterreitmaier, E.; Schuster, M. *Anal. Chim. Acta* 1995, 309, 339-344; Descaizo, A. B.; Martinez-Manez, R.; Radeglia, R.; Rurack, K.; Soto, J. *J. Am. Chem. Soc.* 2003, 125, 3418-3419; Sasaki, D. Y.; Padilla, B. E. *Chem. Commun.* 1998, 1581-1582; Tanaka, M.; Nakamura, M.; Ikeda, T.; Ikeda, K.; Ando, H.; Shibutani, Y.; Yajima, S.; Kimura, K. *J. Org. Chem.* 2001, 66, 7008-7012; Burdette, S. C.; Frederickson, C. J.; Lippard, S. J. *J. Am. Chem. Soc.* 2003, 125, 1778-1787; Nolan, E. M.; Burdette, S. C.; Harvey, J.; Hilderbrand, S. A.; Lippard, S. J. *Unpublished results;* Czarnik, A. W. *Acc. Chem. Res.* 1994, 27, 302-308; Drever, J. I. *The Geochemistry of Natural Waters: Surface and Groundwater Environments* 3$^{rd}$ Ed; Prentice Hall: Upper Saddle River, N.J., 1997; Nolan, E. M.;

Burdette, S. C.; Harvey, J.; Hilderbrand, S. G. *Unpublished results;* Brannon, J. H.; Magde, D. *J. Phys. Chem.* 1978, 82, 705-709; Burdetee, S. C.; Walkup, G. K.; Spingler, B. I.; Tsien, R. Y.; Lippard, S. J. *J. Am. Chem. Soc.* 2001, 123, 7831-7841; U.S. patent applications Ser. Nos. 09/901,466 and 10/124,742.

8. EQUIVALENTS

The invention now being fully described, it will be apparent to one of ordinary skill in the art that many changes and modifications may be made thereto without requiring more than routine experimentation or departing from the spirit or scope of the appended claims.

The specification and examples should be considered exemplary only with the true scope and spirit of the invention suggested by the following claims.

We claim:

1. A fluorescein-based ligand, comprising a ligand having any one of the following structures:

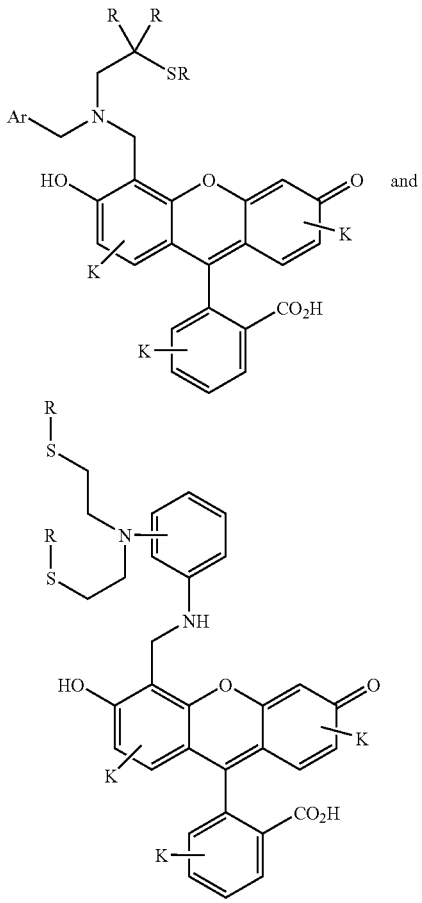

wherein:
Ar represents an aryl ring;
R is, independently for each occurrence, H, alkyl or aryl; and
K is optionally one or more substituents of the indicated aromatic ring, wherein K is independently for each occurrence linear or branched alkyl, alkenyl, linear or branched aminoalkyl, linear or branched acylamino, linear or branched acyloxy, linear or branched alkoxycarbonyl, linear or branched alkoxy, linear or branched alkylaryl, linear or branched hyrdoxyalkyl, linear or branched thioalkyl, acyl, amino, hydroxy, thio, aryloxy, arylalkoxy, hydrogen, alkynyl, halogen, cyano, sulfhydryl, carbamoyl, nitro, trifluoromethyl, amino, thio, lower alkoxy, lower alkylthio, lower alkylamino, nitro, phenoxy, benzyloxy, hydrogen, amine, hydroxyl, alkoxyl, carbonyl, acyl, formyl or sulfonyl.

2. The fluorescein-based ligand of claim 1, wherein upon addition of about 500 nM of said ligand to an aqueous solution containing $Hg^{2+}$ at about 2 ppb and at about pH 7.0, the fluorescence of the fluorescein-based ligand increases by at least about 5%.

3. The fluorescein-based ligand of claim 2, wherein upon addition of about 500 nM of said ligand to an aqueous solution containing $Hg^{2+}$ at about 2 ppb and at about pH 7.0, the fluorescence of the fluorescein-based ligand increases by at least about 10%.

4. The fluorescein-based ligand of claim 3, wherein upon addition of about 500 nM of said ligand to an aqueous solution containing $Hg^{2+}$ at about 2 ppb and at about pH 7.0, the fluorescence of the fluorescein-based ligand increases by at least about 50%.

5. The fluorescein-based ligand of claim 4, wherein upon addition of about 500 nM of said ligand to an aqueous solution containing $Hg^{2+}$ at about 2 ppb and at about pH 7.0, the fluorescence of the fluorescein-based ligand increases by at least about 100%.

6. The fluorescein-based ligand of claim 1, wherein upon addition of about 1 μM of said ligand to an aqueous solution containing $Hg^{2+}$ at about 1 ppm and at about pH 7.0, the fluorescence of the fluorescein-based ligand increases by at least about 5%.

7. The fluorescein-based ligand of claim 1, wherein upon addition of about 1 μM of said ligand to an aqueous solution containing $Hg^{2+}$ at about 10 ppm and at about pH 7.0, the fluorescence of the fluorescein-based ligand increases by at least about 5%.

8. The fluorescein-based ligand of claim 1, wherein the fluorescein structure of said ligand has one or more K substituents at any of the aromatic ring carbon positions.

9. The fluorescein-based ligand of claim 1, wherein said ligand forms a chelating agent upon complexation of said ligand with a metal ion.

10. The fluorescein-based ligand of claim 1, wherein said ligand forms a bidentate or tridentate chelating agent upon said complexation.

11. A coordination complex, comprising a metal ion coordinated to one of the fluorescein-based ligands claimed above.

12. The coordination complex of claim 11, wherein said metal ion is a heavy metal ion.

13. The coordination complex of claim 11, comprising $Hg^{2+}$ coordinated to one of the fluorescein-based ligands claimed above.

* * * * *

UNITED STATES PATENT AND TRADEMARK OFFICE
CERTIFICATE OF CORRECTION

PATENT NO. : 7,615,377 B2
APPLICATION NO. : 10/928924
DATED : November 10, 2009
INVENTOR(S) : Lippard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1443 days.

Signed and Sealed this

Nineteenth Day of October, 2010

David J. Kappos
*Director of the United States Patent and Trademark Office*